US010326067B2

(12) United States Patent
Arnepalli et al.

(10) Patent No.: US 10,326,067 B2
(45) Date of Patent: Jun. 18, 2019

(54) METHODS TO SYNTHESIZE SINGLE SOURCE PRECURSORS AND METHODS TO DEPOSIT NANOWIRE BASED THIN FILMS FOR HIGH EFFICIENCY THERMOELECTRIC DEVICES

(71) Applicant: APPLIED MATERIALS, INC., Santa Clara, CA (US)

(72) Inventors: Ranga Rao Arnepalli, Krishna (IN); Tapash Chakraborty, Mumbai (IN); Robert Jan Visser, Menlo Park, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 632 days.

(21) Appl. No.: 14/852,125

(22) Filed: Sep. 11, 2015

(65) Prior Publication Data
US 2016/0247994 A1 Aug. 25, 2016

(30) Foreign Application Priority Data

Feb. 24, 2015 (IN) .............................. 519/DEL/2015

(51) Int. Cl.
C07F 19/00 (2006.01)
H01L 35/24 (2006.01)
C07F 11/00 (2006.01)
H01L 35/34 (2006.01)

(52) U.S. Cl.
CPC .............. H01L 35/24 (2013.01); C07F 11/00 (2013.01); H01L 35/34 (2013.01)

(58) Field of Classification Search
CPC ............... C07F 19/00; C07F 9/92; C07F 9/94
USPC ..................................................... 556/64, 76
See application file for complete search history.

(56) References Cited

U.S. PATENT DOCUMENTS

2002/0170590 A1 11/2002 Heremans et al.
2014/0262810 A1 9/2014 Rondinone et al.

FOREIGN PATENT DOCUMENTS

KR 10-2011-0037251 A 4/2011

OTHER PUBLICATIONS

Simon, P. et al.: Oxidative addition of diphenyldichalcogenides PhEEPh ( E=S, Se, Te) to low-valent CN- and NCN-chelated organoantimony and organobismuth compounds. Organometallics, vol. 32, pp. 239-248, 2013.*
Zhi-Gang Chen., Guang Han, Lei Yang, Lina Cheng, Jin Zou Progress in Natural Science: Materials International 2012;22(6):535-549.

Y. Pei, X. Shi, A. LaLonde, H. Wang, L. Chen, G.J. Snyder, Nature 473 (2011) 66-69.
J.R. Sootsman, D.Y. Chung, M.G. Kanatzidis, Angewandte Chemie, International Edition 48 (2009) 8616-8639.
G.J. Snyder, E.S. Toberer, Nature Materials 7 (2008) 105-114.
H. Bottner, G. Chen, R. Venkatasubramanian, MRS Bulletin 31 (2006) 211-217.
A.J. Minnich, M.S. Dresselhaus, Z.F. Ren, G. Chen, Energy & Environmental Science 2 (2009) 466-479.
Y.C. Lan, A.J. Minnich, G. Chen, Z.F. Ren, Advanced Functional Materials 20 (2010) 357-376.
T.C. Harman, P.J. Taylor, M.P. Walsh, B.E. LaForge, Science (New York, NY) 297 (2002) 2229-2232.
A.I. Hochbaum, R. Chen, R.D. Delgado, W. Liang, E.C. Garnett, M. Najarian, et al., Nature 451 (2008) 163-U165.
B. Poudel, Q. Hao, Y. Ma, Y. Lan, A. Minnich, B. Yu, et al., Science (New York, NY) 320 (2008) 634-638.
J.P. Heremans, V. Jovovic, E.S. Toberer, A. Saramat, K. Kurosaki, A. Charoenphakdee, et al., Science (New York, NY) 321 (2008) 554-557.
X.W. Wang, H. Lee, Y.C. Lan, G.H. Zhu, G. Joshi, D.Z. Wang, et al., Applied Physics Letters 93 (2008) 193121.
C.J. Vineis, A. Shakouri, A. Majumdar, M.G. Kanatzidis, Advanced Materials 22 (2010) 3970-3980.
P. Vaqueiro, A.V. Powell, Journal of Materials Chemistry 20 (2010) 9577-9584.
S.K. Bux, J.P. Fleurial, R.B. Kaner, Chemical Communications 46 (2010) 8311-8324.
M.G. Kanatzidis, Chemistry of Materials 22 (2009) 648-659.
P. Pichamusakorn, P. Bandaru, Materials Science and Engineering: R: Reports 67 (2010) 19-6.
J.R. Szczech, J.M. Higgins, S. Jin, Journal of Materials Chemistry 21 (2011) 4037-4055.
M.S. Dresselhaus, G. Chen, M.Y. Tang, R.G. Yang, H. Lee, D.Z. Wang, et al., Advanced Materials 19 (2007) 1043-1053.
L.D. Hicks, T.C. Harman, X. Sun, M.S. Dresselhaus, Physical Review B 53 (1996) R10493.
A. Mavrokefalos, A.L. Moore, M.T. Pettes, L. Shi, W. Wang, X. Li, Journal of Applied Physics 105 (2009) 104318.
I. Chowdhury, R. Prasher, K. Lofgreen, G. Chrysler, S. Narasimhan, R. Mahajan, et al., Nature Nanotechnology, 4 (2009) 235-238.
Klammer, J., et al., "Elecrochemical Route to Thermoelectric Nanowires Via Organic Electrolytes", Phys. Status Solidi B 247, No. pp. 1384-1392 (2010).
International Search Report and Written Opinion dated May 27, 2016 for PCT Application No. PCT/US2016/018986.

* cited by examiner

Primary Examiner — Charanjit Aulakh
(74) Attorney, Agent, or Firm — Moser Taboada; Alan Taboada

(57) ABSTRACT

Single source precursors, methods to synthesize single source precursors and methods to deposit nanowire based thin films using single source precursors for high efficiency thermoelectric devices are provided herein. In some embodiments, a method of forming a single source precursor includes mixing a first compound with one of $SbX_3$, $SbX_5$, $Sb_2(SO_4)_3$ or with one of $BiX_3$, $Bi(NO_3)_3$, $Bi(OTf)_3$, $Bi(PO_4)$, $Bi(OAc)_3$, wherein the first compound is one of a lithium selenolate, a lithium tellurolate, a monoselenide, or a monotelluride.

11 Claims, 15 Drawing Sheets (Scheme 1)

(Scheme 2)

(Scheme 3)

(Scheme 6)

(Scheme 10)

(Scheme 11)

(Scheme 13)

METHODS TO SYNTHESIZE SINGLE SOURCE PRECURSORS AND METHODS TO DEPOSIT NANOWIRE BASED THIN FILMS FOR HIGH EFFICIENCY THERMOELECTRIC DEVICES

CROSS-REFERENCE TO RELATED APPLICATIONS

This application claims benefit of Indian patent application number 519/DEL/2015, filed Feb. 24, 2015, which is herein incorporated by reference in its entirety.

FIELD

Embodiments of the present disclosure generally relate to substrate processing systems and methods, and more particularly to single source precursors, methods to synthesize single source precursors and methods to deposit nanowire based thin films using single source precursors for high efficiency thermoelectric devices.

BACKGROUND

Bismuth tellurium ($Bi_2Te_3$) and alloys of Bismuth tellurium ($Bi_2Te_3$), along with bismuth selenium ($Bi_2Se_3$), antimony tellurium ($Sb_2Te_3$) and antimony selenium ($Sb_2Se_3$) are the best materials for thermoelectric applications at approximately room temperature. These materials are narrow band gap semiconductors with a layered structure and a high figure of merit Z. Thin films of bismuth tellurium ($Bi_2Te_3$) have been deposited by various methods including metal oxide chemical vapor deposition (MOCVD), RF diode sputtering, molecular beam epitaxy, flash evaporation, electrodeposition and hot-wire epitaxy through a dual source approach. The precursors used for deposition of bismuth tellurium ($Bi_2Te_3$) include $Bi(CH_3)_3$, $Bi(C_2H_5)_3$, $Bi(N(Si(CH_3)_3)_2)_3$ and $Bi(NMe_2)_3$ as sources of bismuth and $Te(CH_3)_2$, $Te(C_2H_5)_2$, $Te(CH(CH_3)_2)_2$, $Te(C(CH_3)_3)_2$ and $Te(SiMe_3)_2$ as sources of tellurium. The dual source approach can be improved upon by application of a single source approach to advantageously provide (a) air and/or moisture stability, (b) low temperature film growth, (c) control of stoichiometry, (d) limitation of side reactions, and (e) control of impurity incorporation into films by proper ligand design.

Accordingly, the inventors have developed improved single source precursors, methods for synthesizing single source precursors and methods to deposit nanowire based thin films using single source precursors for high efficiency thermoelectric devices.

SUMMARY

Embodiments of the present disclosure relate to a compound having the following formula:

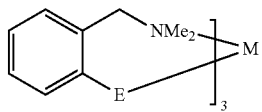

(a)

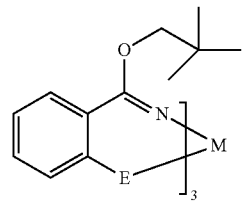

(b)

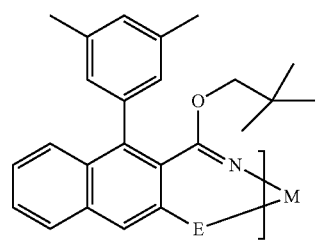

(c)

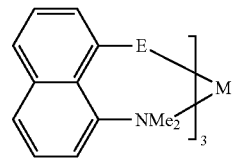

(d)

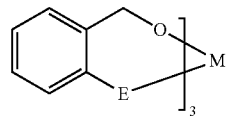

(e)

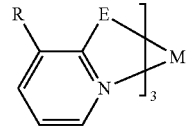

(f)

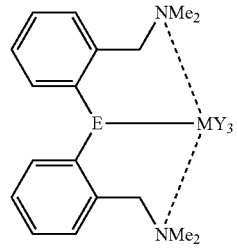

(g)

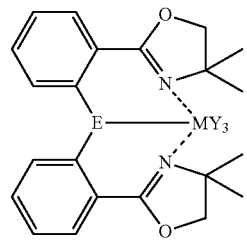

(h)

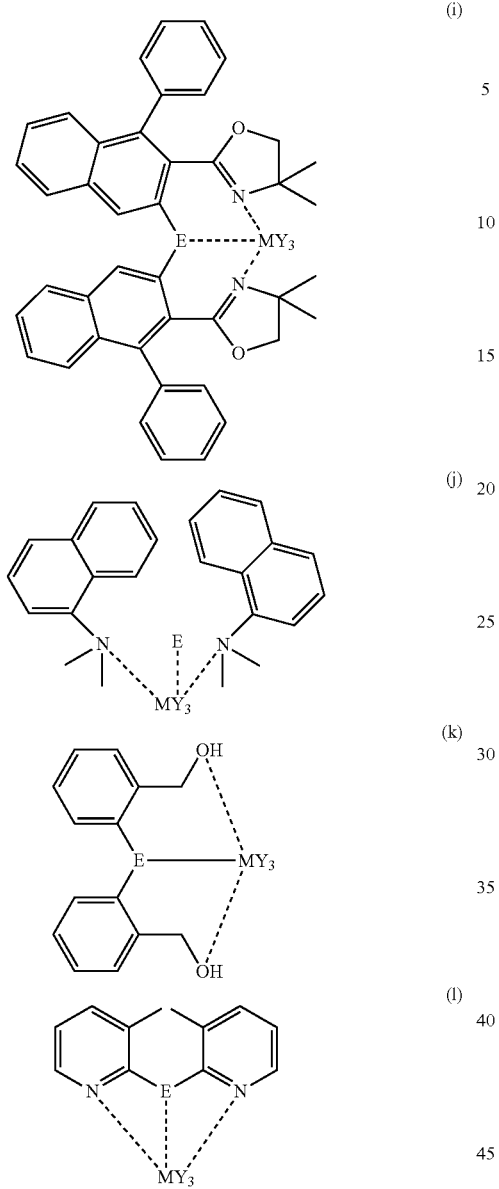
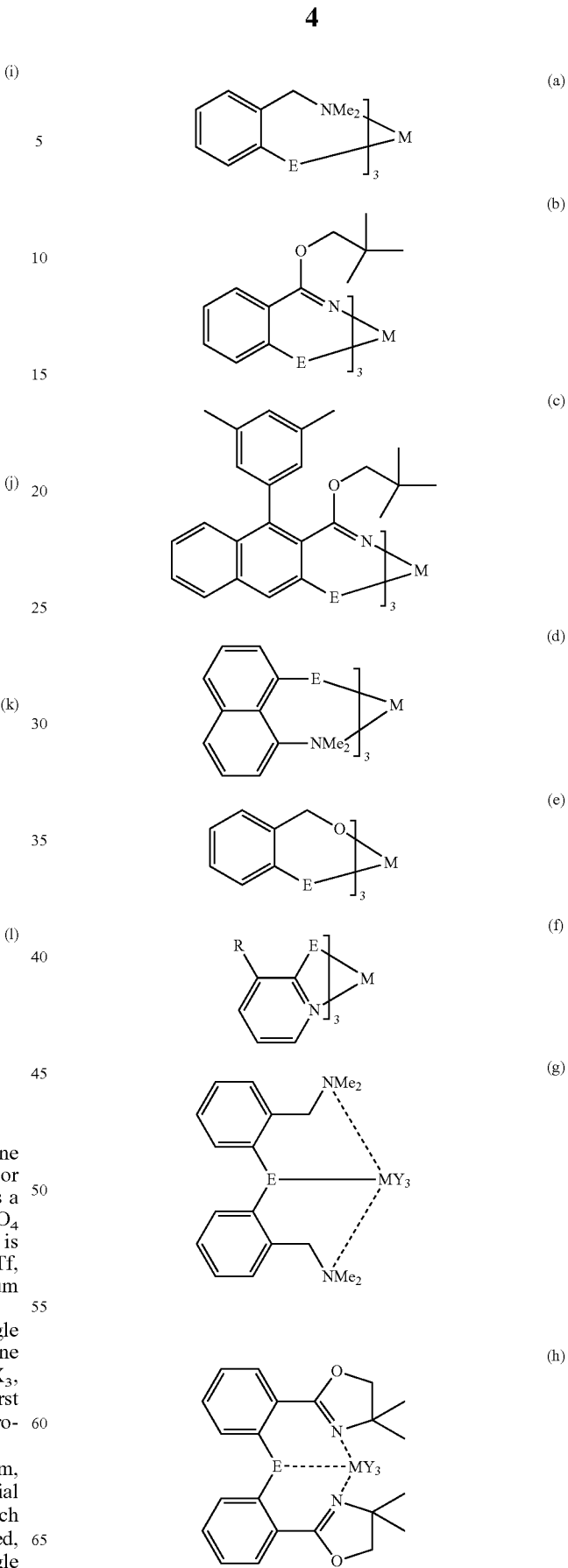

wherein E is one of tellurium (Te) or selenium (Se), M is one of bismuth (Bi) or antimony (Sb), R is one of hydrogen or an alkyl having a general formula $C_nH_{2n+1}$, wherein n is a whole number, and wherein Y is one of a halogen or $SO_4$ when E is one of tellurium (Te) or selenium (Se) and M is antimony (Sb) or wherein Y is one of a halogen, $NO_3$, OTf, $PO_4$, or OAc when E is one of tellurium (Te) or selenium (Se) and M is bismuth (Bi).

In some embodiments, a method of forming a single source precursor, includes mixing a first compound with one of one of $SbX_3$, $SbX_5$, $Sb_2(SO_4)_3$ or with one of $BiX_3$, $Bi(NO_3)_3$, $Bi(OTf)_3$, $Bi(PO_4)$, $Bi(OAc)_3$, wherein the first compound is one of a lithium selenolate, a lithium tellurolate, a monoselenide, or a monotelluride.

In some embodiments, a method for depositing a film, includes flowing a liquid polymer precursor material through an orifice spaced apart from a substrate upon which the liquid polymer precursor material is to be deposited, wherein the liquid polymer precursor comprises a single source precursor having one of the following formulas:

-continued

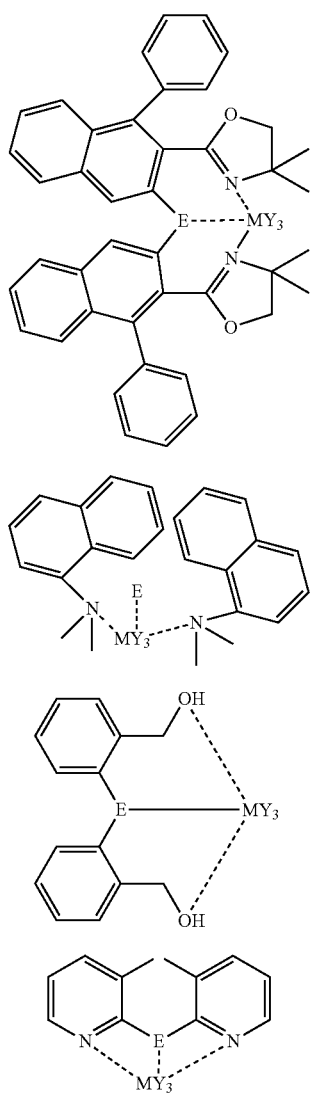

wherein E is one of tellurium (Te) or selenium (Se), M is one of bismuth (Bi) or antimony (Sb), and R is one of hydrogen or an alkyl having a general formula $C_nH_{2n+1}$, wherein n is a whole number, and wherein Y is one of a halogen or $SO_4$ when E is one of tellurium (Te) or selenium (Se) and M is antimony (Sb) or wherein Y is one of a halogen, $NO_3$, OTf, $PO_4$, or OAc when E is one of tellurium (Te) or selenium (Se) and M is bismuth (Bi); providing a potential difference between the orifice and the substrate to attract the liquid polymer towards the substrate and form a deposited material on the substrate; and curing the deposited material.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

Figure 1:
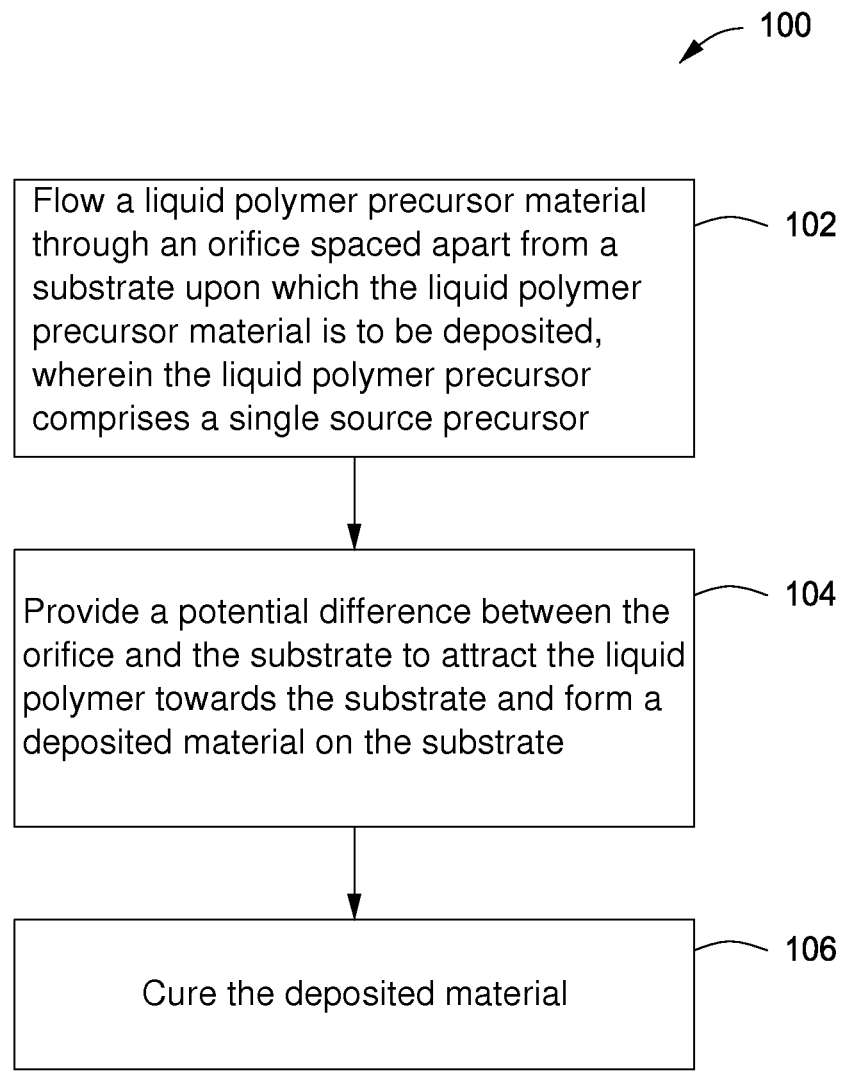
FIG. 1 is a flow diagram of a method for depositing polymer films in accordance with some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Single source precursors, methods to synthesize single source precursors and methods to deposit nanowire based thin films using single source precursors for high efficiency thermoelectric devices are provided herein. Embodiments of the present disclosure provide single source precursors and methods to synthesize single source precursors that can be used advantageously over a conventional dual source approach for the following reasons a) air and/or moisture stability, b) low temperature film growth, c) control of stoichiometry, d) limitation of side reactions, e) control of impurity incorporation into films by proper ligand design.

Bismuth tellurium ($Bi_2Te_3$) and alloys of Bismuth tellurium ($Bi_2Te_3$), along with bismuth selenium ($Bi_2Se_3$), antimony tellurium ($Sb_2Te_3$) and antimony selenium ($Sb_2Se_3$) are preferred materials for thermoelectric applications at approximately room temperature. Typically, bismuth tellurium ($Bi_2Te_3$) and the other films listed above have been grown by metal oxide chemical vapor deposition (MOCVD) using dual precursors. However, the inventors have observed that a single source precursor (SSP) can be used advantageously over a conventional dual source approach for the following reasons (a) air and/or moisture stability, (b) low temperature growth, (c) control of stoichiometry, (d) limited side reactions, (e) control impurity incorporation into films by proper ligand design. However, SSPs for bismuth tellurides are very rare owing to air and moisture sensitivity, reactivity, thermal instability of the compounds and difficulty in isolation. Bismuth complexes of organotellurides can be classified into two types: (a) one in which the bismuth is coordinated to neutral telluroether ligands and (b) another in which the bismuth is coordinated to anionic tellurolate ligands. The inventors have observed that bismuth complexes of the later type provide stronger bismuth-telluride bonds.

Furthermore, organotellurolates of bismuth complexes can be synthesized by taking advantages of proper ligand design. There are two approaches to stabilize by ligand design otherwise unstable compounds: a) one is the introduction of bulky substituents on the ligand to protect the reactive center (Bi—Te bond) and b) another is the introduction of intramolecular secondary bonding interactions at the reactive center. Bi/Sb telluride/selenide SSPs can be synthesized by the methods as given in the attached scheme.

Embodiments of the disclosure provide methods of synthesizing these complexes as SSPs for bismuth tellurium ($Bi_2Te_3$) along with SSPs for related complexes such as bismuth selenium ($Bi_2Se_3$), antimony selenium ($Sb_2Se_3$) and antimony tellurium ($Sb_2Te_3$).

The following formula depicts a single source precursor (SSP) in accordance with some embodiments of the present disclosure:

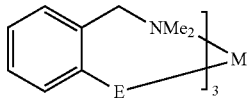

Figure 3:
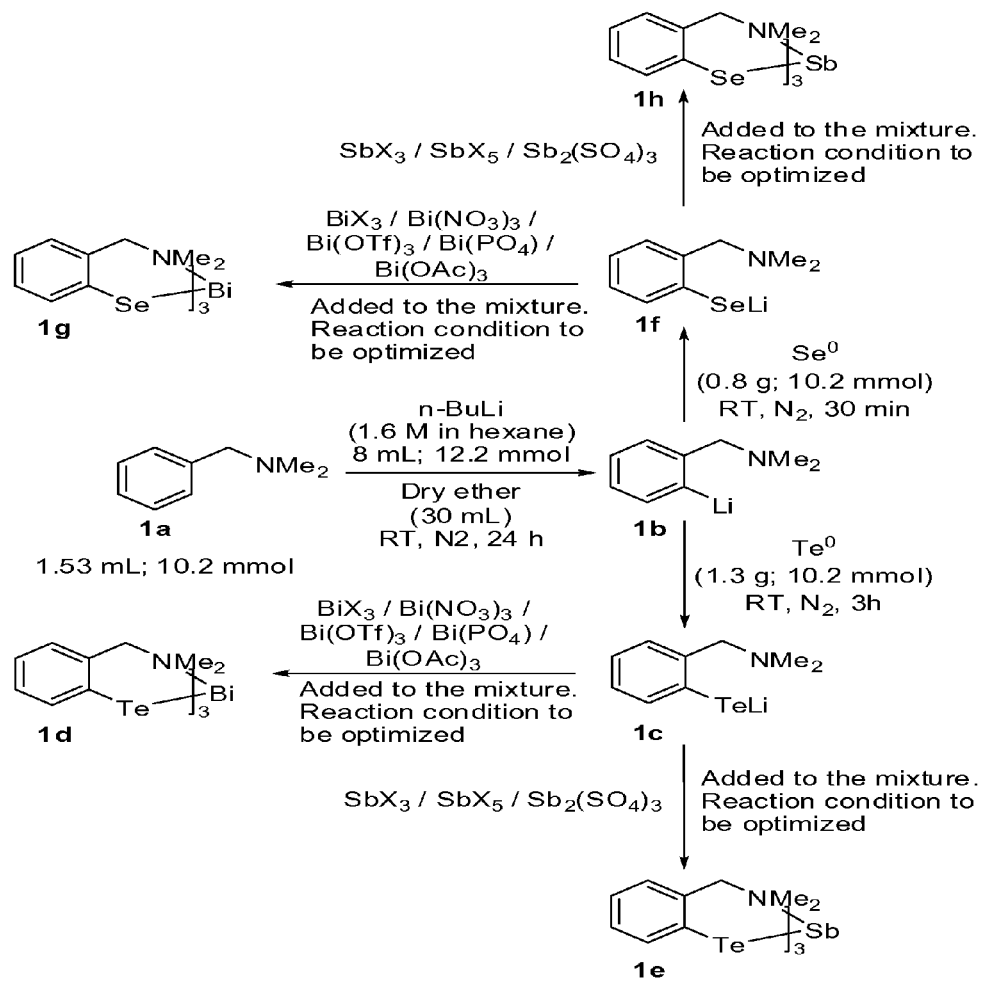
FIG. 3 depicts a scheme (Scheme 1) for forming a single source precursor in accordance with some embodiments of the present disclosure.

In some embodiments, E is one of tellurium (Te) or selenium (Se) and M is one of bismuth (Bi) or antimony (Sb). In some embodiments, the SSP described above is formed via Scheme 1, as depicted in FIG. 3.

As depicted in Scheme 1 (FIG. 3), a starting compound 1a is used to form intermediary compound 1b. Starting compound 1a is a commercially available N,N-dimethylbenzenemethanamine. Intermediary compound. 1b is 2-lithium-N,N-dimethylbenzenemethanamine. As described in Scheme 1, intermediary compound 1b can be used to form either lithium selenolate 1f or lithium tellurolate 1c. Lithium selenolate 1f is formed as shown in Scheme 1 via the addition of selenium (Se) to intermediary compound 1b. Lithium tellurolate 1c is formed as shown in Scheme 1 via the addition of tellurium (Te) to intermediary compound 1b. One of $SbX_3$, $SbX_5$, $Sb_2(SO_4)_3$ is added to the lithium selenolate 1f to form a selenolate antimony SSP 1h. One of $SbX_3$, $SbX_5$, $Sb_2(SO_4)_3$ is added to the lithium tellurolate 1c to form a tellurolate antimony SSP 1e. One of $BiX_3$, $Bi(NO_3)_3$, $Bi(OTf)_3$, $Bi(PO_4)$, $Bi(OAc)_3$ is added to the lithium selenolate 1f to form a selenolate bismuth SSP 1g. One of $BiX_3$, $Bi(NO_3)_3$, $Bi(OTf)_3$, $Bi(PO_4)$, $Bi(OAc)_3$ is added to the lithium tellurolate 1c to form a tellurolate bismuth SSP 1d. The inventors have observed that suitable reaction conditions for the formation of the selenolate antimony SSP 1h, the tellurolate antimony SSP 1e, the selenolate bismuth SSP 1g, and the tellurolate bismuth SSP 1d, include a temperature of about −78 degrees Celsius to about 200 degrees Celsius, utilization of suitable solvents such as hexane, pentane, diethylether, and THF. Purification of the SSPs 1d, 1e, 1g, and 1h utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 1d, 1e, 1g, and 1h in Scheme 1.

The following formula depicts a single source precursor (SSP) in accordance with some embodiments of the present disclosure:

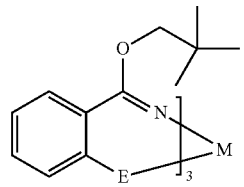

Figure 4:
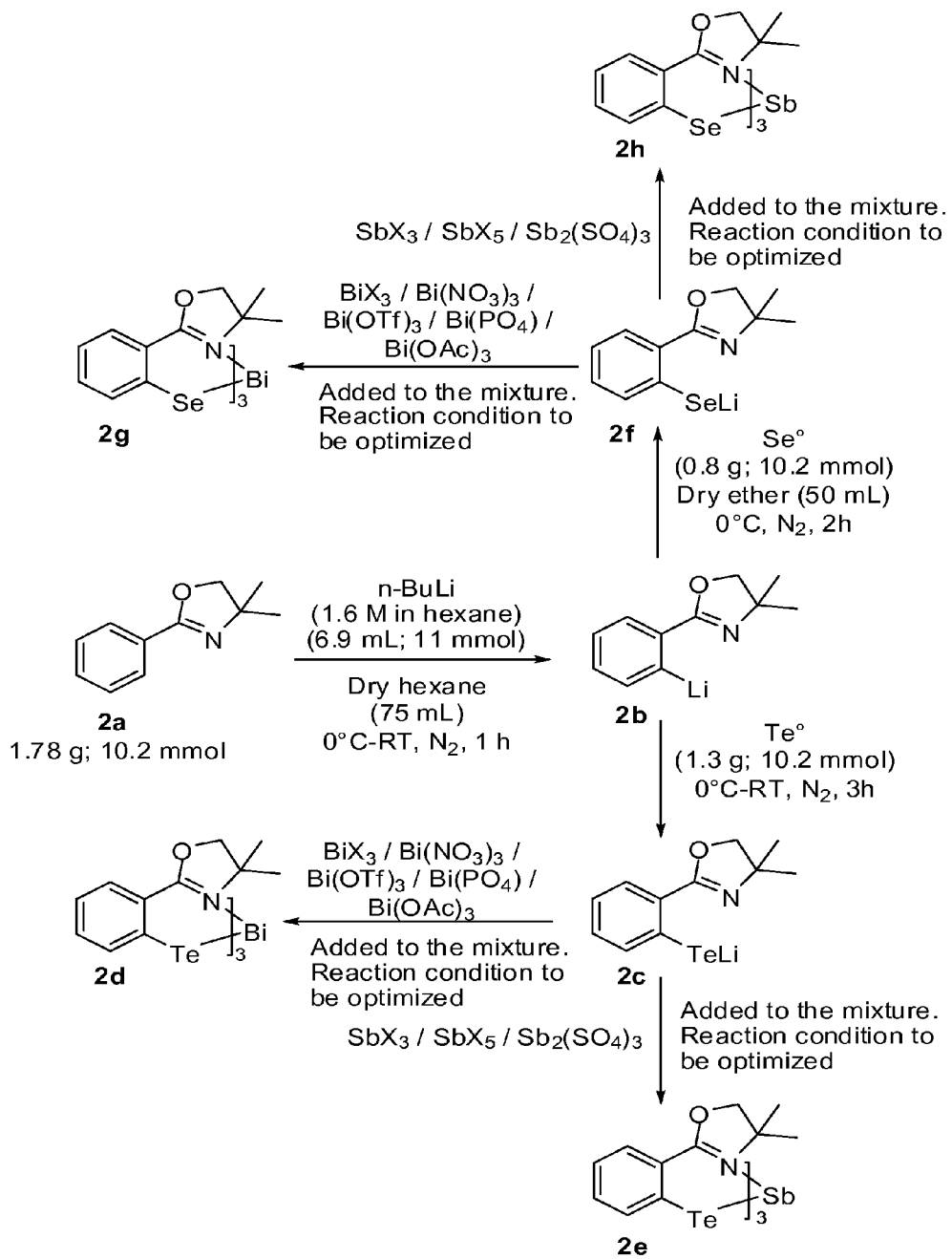
FIG. 4 depicts a scheme (Scheme 2) for forming a single source precursor in accordance with some embodiments of the present disclosure.

In some embodiments, E is one of tellurium (Te) or selenium (Se) and M is one of bismuth (Bi) or antimony (Sb). In some embodiments, the SSP described above is formed via Scheme 2, as depicted in FIG. 4.

As depicted in Scheme 2 (FIG. 4), a starting compound 2a is used to form intermediary compound 2b. Starting compound 2a is a commercially available 4,5-dihydro-4,4-dimethyl-2-phenyl-oxazole. Intermediary Compound 2b is [2-(4,5-dihydro-4,4-dimethyl-2-oxazolyl)phenyl] lithium. As described in Scheme 2, intermediary compound 2b can be used to form either lithium selenolate 2f or lithium tellurolate 2c. Lithium selenolate 2f is formed as shown in Scheme 2 via the addition of selenium (Se) to intermediary compound 2b. Lithium tellurolate 2c is formed as shown in Scheme 2 via the addition of tellurium (Te) to intermediary compound 2b. One of $SbX_3$, $SbX_5$, $Sb_2(SO_4)_3$ is added to the lithium selenolate 2f or the lithium tellurolate 2c to form a selenolate antimony SSP 2h or a tellurolate antimony SSP 2e respectively. One of $BiX_3$, $Bi(NO_3)_3$, $Bi(OTf)_3$, $Bi(PO_4)$, $Bi(OAc)_3$ is added to the lithium selenolate 2f or the lithium tellurolate 2c to form a selenolate bismuth SSP 2g or a tellurolate bismuth SSP 2d respectively. The inventors have observed that suitable reaction conditions for the formation of the selenolate antimony SSP 2h, the tellurolate antimony SSP 2e, the selenolate bismuth SSP 2g, and the tellurolate bismuth SSP 2d, include a temperature of about −78 degrees Celsius to about 200 degrees Celsius, utilization of suitable solvents such as hexane, pentane, diethylether, and THF. Purification of the SSPs 2d, 2e, 2g, and 2h utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 2d, 2e, 2g, and 2h in Scheme 2.

The following formula depicts a single source precursor (SSP) in accordance with some embodiments of the present disclosure:

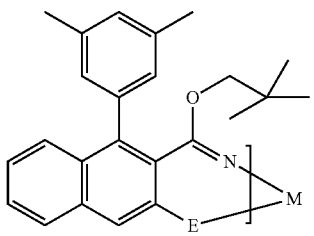

Figure 5:
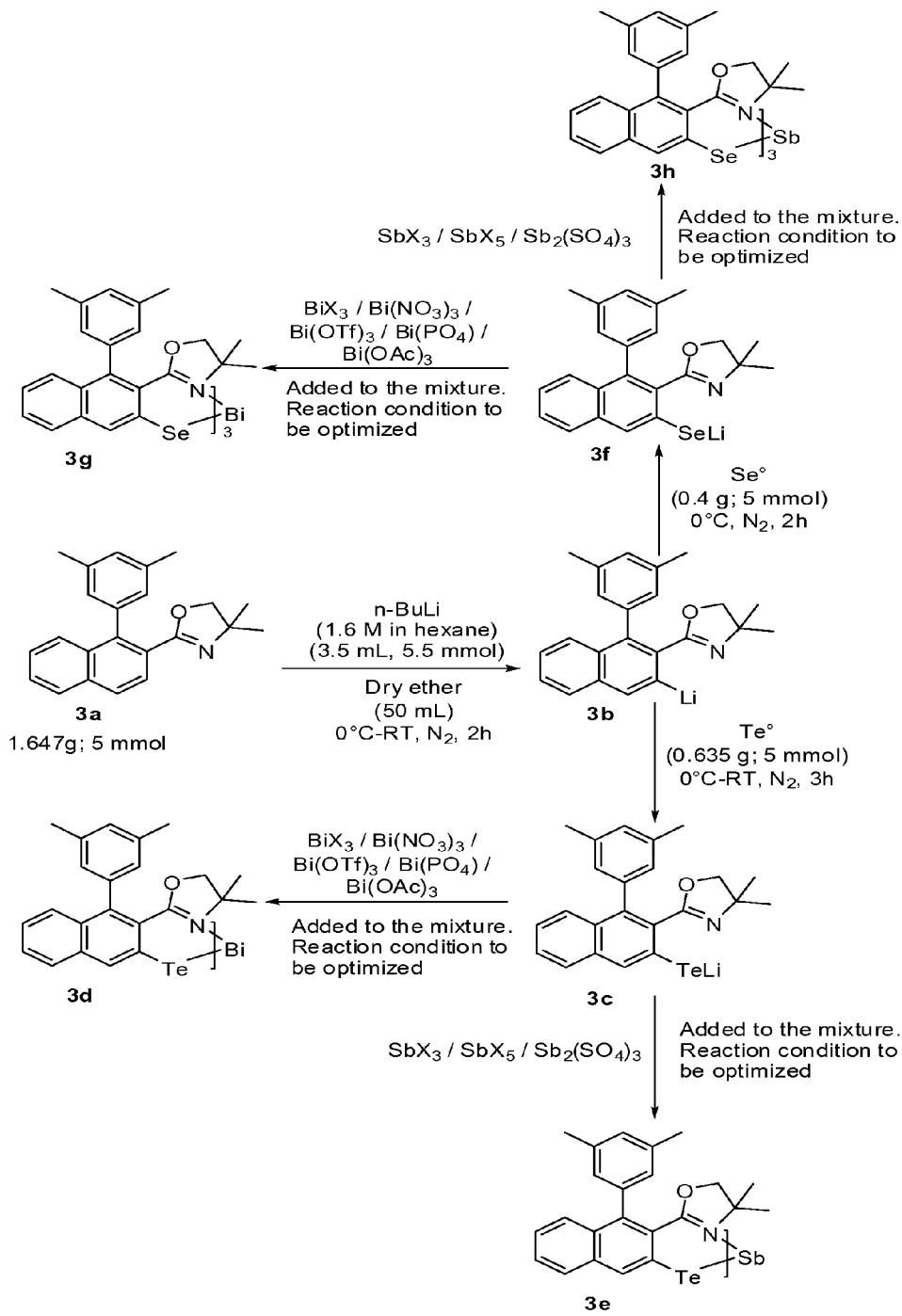
FIG. 5 depicts a scheme (Scheme 3) for forming a single source precursor in accordance with some embodiments of the present disclosure.

In some embodiments, E is one of tellurium (Te) or selenium (Se) and M is one of bismuth (Bi) or antimony (Sb). In some embodiments, the SSP described above is formed via Scheme 3, as depicted in FIG. 5.

As depicted in Scheme 3 (FIG. 5), a starting compound 3a is used to form intermediary compound 3b. Starting compound 3a is commercially available 2-[1-(3,5-dimethylphenyl)-2-naphthalenyl]-4,5-dihydro-4,4-dimethyl-oxazole. Intermediary compound 3b is 2-[2-[1-(3,5-dimethylphenyl)-2-naphthalenyl]-4,5-dihydro-4,4-dimethyl-oxazolyl)phenyl] lithium. As described in Scheme 3, intermediary compound 3b can be used to form either lithium selenolate 3f or lithium tellurolate 3c. Lithium selenolate 3f is formed as shown in Scheme 3 via the addition of selenium (Se) to intermediary compound 3b. Lithium tellurolate 3c is formed as shown in Scheme 3 via the addition of tellurium (Te) to intermediary compound 3b. One of SbX$_3$, SbX$_5$, Sb$_2$(SO$_4$)$_3$ is added to the lithium selenolate 3f or the lithium tellurolate 3c to form a selenolate antimony SSP 3h or a tellurolate antimony SSP 3e respectively. One of BiX$_3$, Bi(NO$_3$)$_3$, Bi(OTf)$_3$, Bi(PO$_4$), Bi(OAc)$_3$ is added to the lithium selenolate 3f or the lithium tellurolate 3c to form a selenolate bismuth SSP 3g or a tellurolate bismuth SSP 3d respectively. The inventors have observed that suitable reaction conditions for the formation of the selenolate antimony SSP 3h, the tellurolate antimony SSP 3e, the selenolate bismuth SSP 3g, and the tellurolate bismuth SSP 3d, include a temperature of about −78 degrees Celsius to about 200 degrees Celsius, utilization of suitable solvents such as hexane, pentane, diethylether, and THF. Purification of the SSPs 3d, 3e, 3g, and 3h utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 3d, 3e, 3g, and 3h in Scheme 3.

The following formula depicts a single source precursor (SSP) in accordance with some embodiments of the present disclosure:

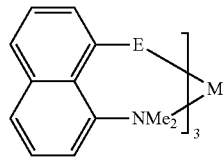

Figure 6:
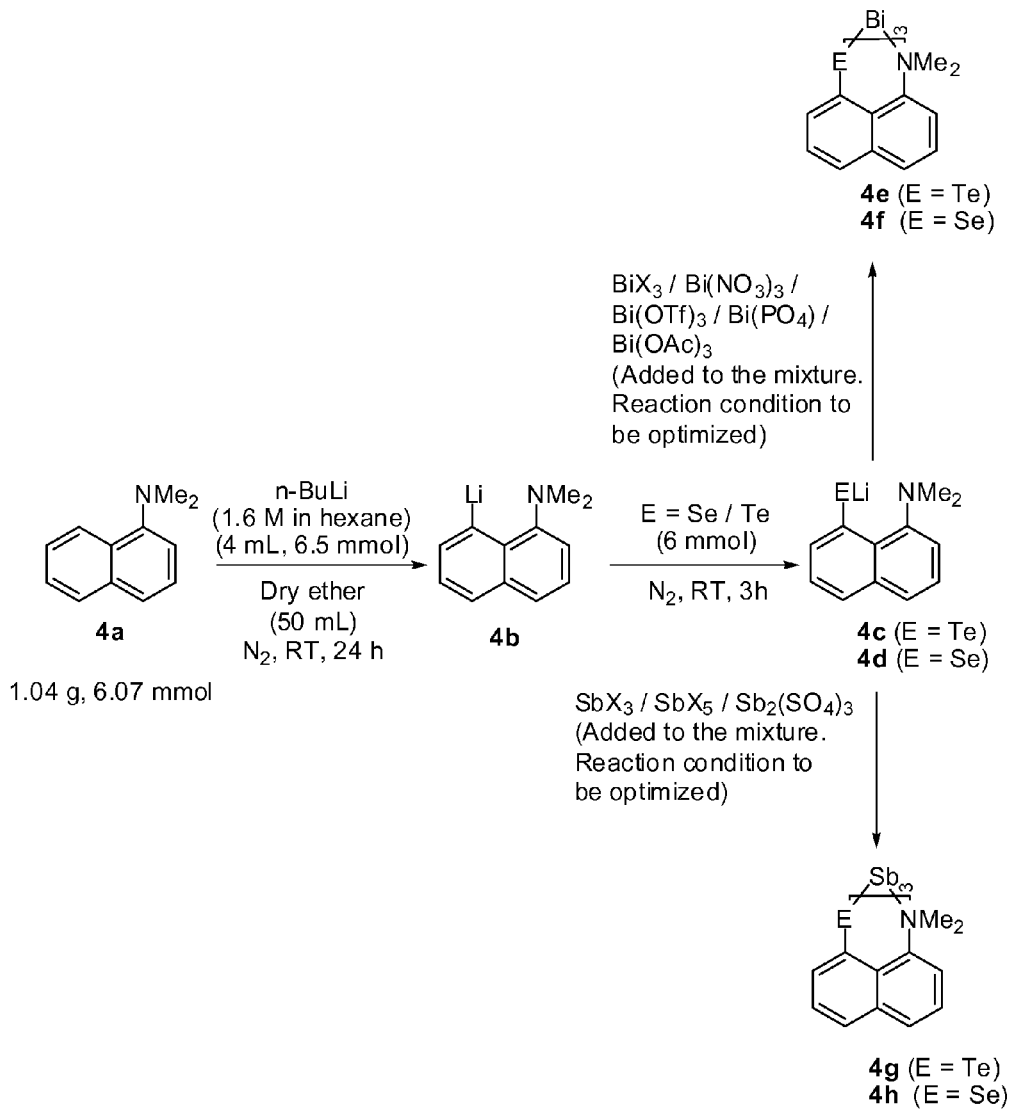
FIG. 6 depicts a scheme (Scheme 4) for forming a single source precursor in accordance with some embodiments of the present disclosure.

In some embodiments, E is one of tellurium (Te) or selenium (Se) and M is one of bismuth (Bi) or antimony (Sb). In some embodiments, the SSP described above is formed via Scheme 4, as depicted in FIG. 6.

As depicted in Scheme 4 (FIG. 6), a starting compound 4a is used to form intermediary compound 4b. Starting compound 4a is commercially available N,N-dimethyl-1-naphthanamine. Intermediary compound 4b is (8-dimethylamino)-1-naphthyllithium. As described in Scheme 4, intermediary compound 4b can be used to form either lithium tellurolate 4c or lithium selenolate 4d. Lithium selenolate 4d is formed as shown in Scheme 4 via the addition of selenium (Se) to intermediary compound 4b. Lithium tellurolate 4c is formed as shown in Scheme 4 via the addition of tellurium (Te) to intermediary compound 4b. One of SbX$_3$, SbX$_5$, Sb$_2$(SO$_4$)$_3$ is added to either the lithium tellurolate 4c or the lithium selenolate 4d to form a tellurolate antimony SSP 4g or a selenolate antimony SSP 4h respectively. One of BiX$_3$, Bi(NO$_3$)$_3$, Bi(OTf)$_3$, Bi(PO$_4$), Bi(OAc)$_3$ is added to either the lithium tellurolate 4c or the lithium selenolate 4d to form a tellurolate bismuth SSP 4e or a selenolate bismuth SSP 4f respectively. The inventors have observed that suitable reaction conditions for the formation of the selenolate antimony SSP 4h, the tellurolate antimony SSP 4g, the selenolate bismuth SSP 4f, and the tellurolate bismuth SSP 4e, include a temperature of about −78 degrees Celsius to about 200 degrees Celsius, utilization of suitable solvents such as hexane, pentane, diethylether, and THF. Purification of the SSPs 4h, 4g, 4e, and 4f utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 4e, 4f, 4g, and 4h in Scheme 4.

The following formula depicts a single source precursor (SSP) in accordance with some embodiments of the present disclosure:

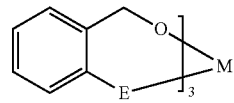

Figure 7:
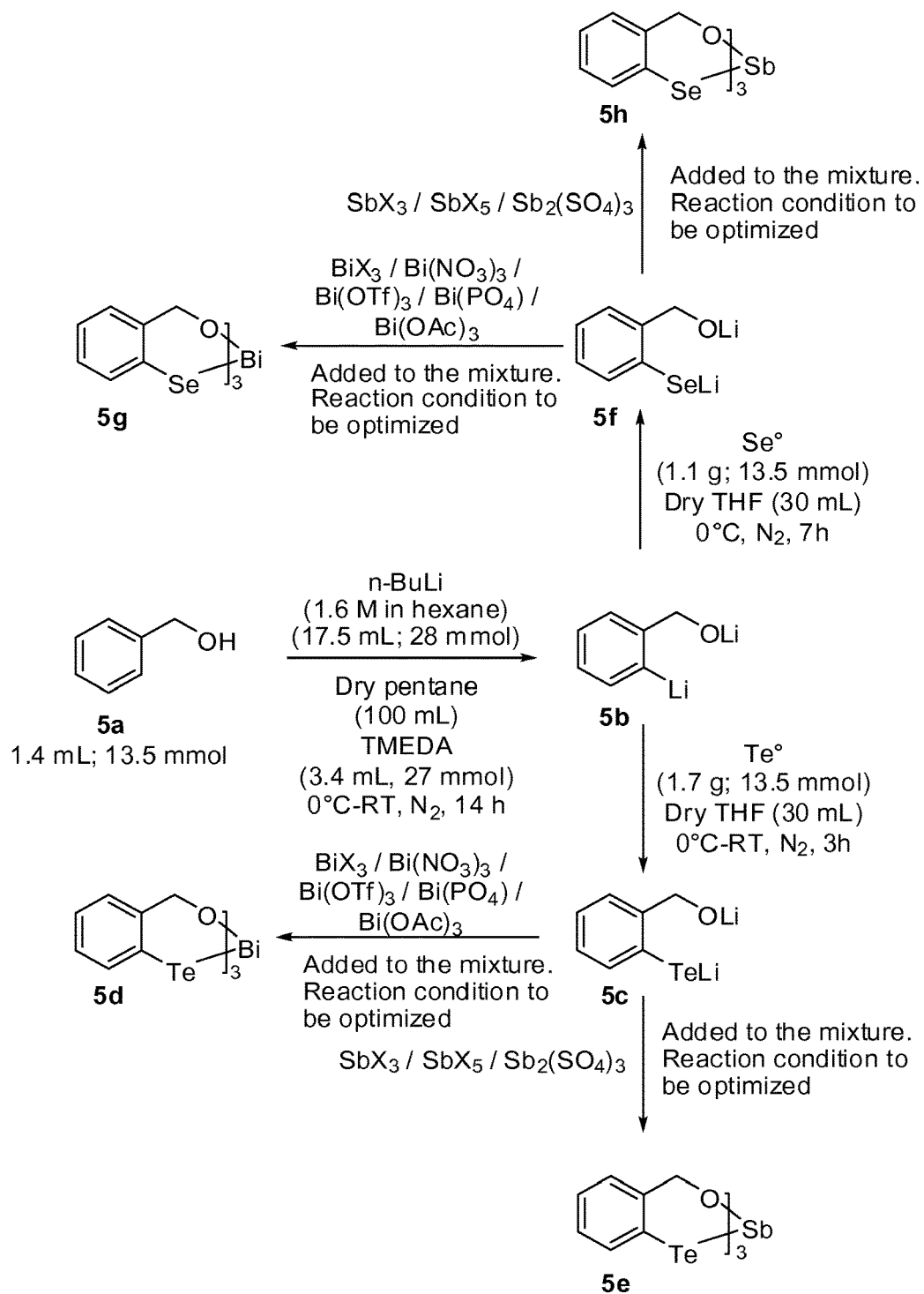
FIG. 7 depicts a scheme (Scheme 5) for forming a single source precursor in accordance with some embodiments of the present disclosure.

In some embodiments, E is one of tellurium (Te) or selenium (Se) and M is one of bismuth (Bi) or antimony (Sb). In some embodiments, the SSP described above is formed via Scheme 5, as depicted in FIG. 7.

As depicted in Scheme 5 (FIG. 7), a starting compound 5a is used to form intermediary compound 5b. Starting compound 5a is commercially available benzyl alcohol. Intermediary compound 5b is lithium salt of [2-(hydroxymethyl)phenyl] lithium. As described in Scheme 5, intermediary compound 5b can be used to form either lithium tellurolate 5c or lithium selenolate 5f. Lithium selenolate 5f is formed as shown in Scheme 5 via the addition of selenium (Se) to intermediary compound 5b. Lithium tellurolate 5c is formed as shown in Scheme 5 via the addition of tellurium (Te) to intermediary compound 5b. One of SbX$_3$, SbX$_5$, Sb$_2$(SO$_4$)$_3$ is added to either the lithium selenolate 5f or the lithium tellurolate 5c to form a selenolate antimony SSP 5h or a tellurolate antimony SSP 5e. One of BiX$_3$, Bi(NO$_3$)$_3$, Bi(OTf)$_3$, Bi(PO$_4$), Bi(OAc)$_3$ is added to either the lithium selenolate 5f or the lithium tellurolate 5c to form a selenolate bismuth SSP 5g or a tellurolate bismuth SSP 5d respectively. The inventors have observed that suitable reaction conditions for the formation of the selenolate antimony SSP 5h, the tellurolate antimony SSP 5e, the selenolate bismuth SSP 5g, and the tellurolate bismuth SSP 5d, include a temperature of about −78 degrees Celsius to about 200 degrees Celsius, utilization of suitable solvents such as hexane, pentane, diethylether, and THF. Purification of the SSPs 5d, 5e, 5g, and 5h utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 5d, 5e, 5g, and 5h in Scheme 5.

The following formula depicts a single source precursor (SSP) in accordance with some embodiments of the present disclosure:

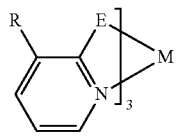

Figure 8:
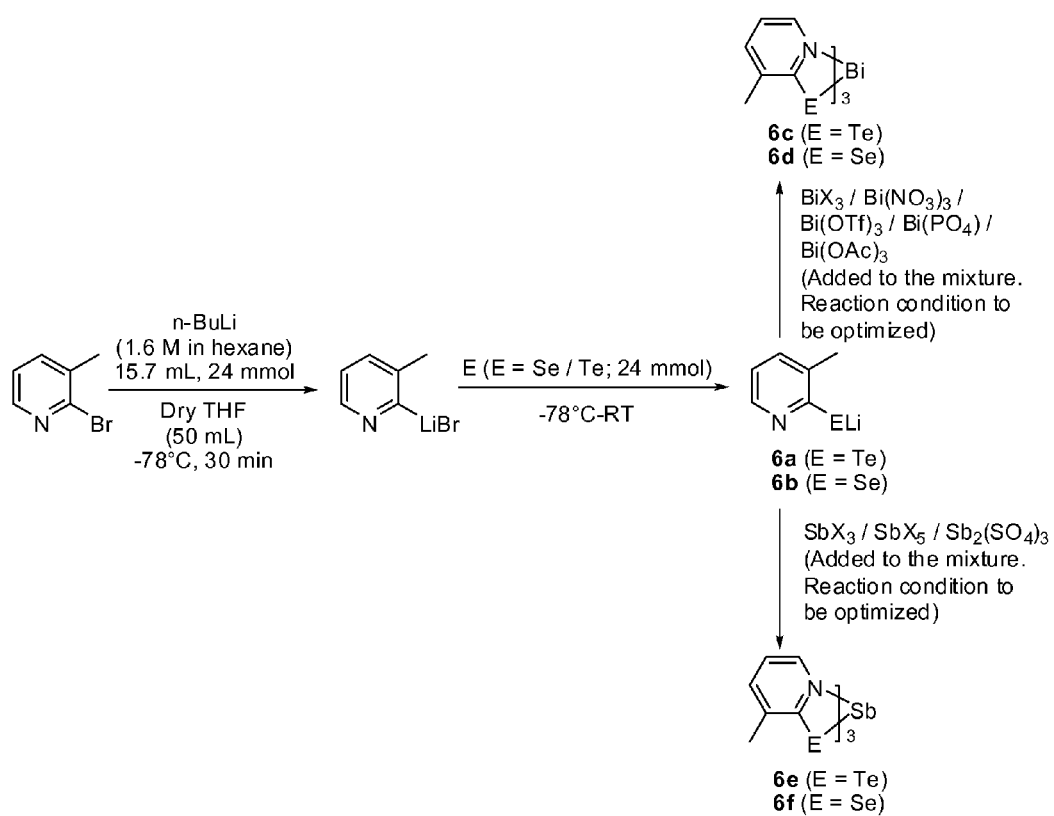
FIG. 8 depicts a scheme (Scheme 6) for forming a single source precursor in accordance with some embodiments of the present disclosure.

In some embodiments, E is one of tellurium (Te) or selenium (Se), M is one of bismuth (Bi) or antimony (Sb) and R is one of hydrogen or an alkyl having the general formula $C_nH_{2n+1}$ and where n is a whole number, such as methyl, $CH_3$, ethyl ($C_2H_5$), propyl ($C_3H_7$), butyl ($C_4H_9$), pentyl ($C_5H_{11}$), or the like. In some embodiments, the SSP described above is formed via Scheme 6, as depicted in FIG. 8.

As depicted in Scheme 6 (FIG. 8), a starting compound 6g is used to form intermediary compound 6h. Starting compound 6g is commercially available 2-bromo-3-methyl-pyridine. Intermediary compound 6h is (2-bromo-3-pyridinyl)-lithium. 6g is commercially available. As described in Scheme 6, intermediary compound 6h can be used to form either lithium tellurolate 6a or lithium selenolate 6b. Lithium selenolate 6b is formed as shown in Scheme 6 via the addition of selenium (Se) to intermediary compound 6h. Lithium tellurolate 6a is formed as shown in Scheme 6 via the addition of tellurium (Te) to intermediary compound 6h. One of $SbX_3$, $SbX_5$, $Sb_2(SO_4)_3$ is added to either the lithium tellurolate 6a or the lithium selenolate 6b to form a tellurolate antimony SSP 6e or a selenolate antimony SSP 6f respectively. One of $BiX_3$, $Bi(NO_3)_3$, $Bi(OTf)_3$, $Bi(PO_4)$, $Bi(OAc)_3$ is added to either the lithium tellurolate 6a or the lithium selenolate 6b to form a tellurolate bismuth SSP 6c or a selenolate bismuth SSP 6d respectively. The inventors have observed that suitable reaction conditions for the formation of the selenolate antimony SSP 6f, the tellurolate antimony SSP 6e, the selenolate bismuth SSP 6d, and the tellurolate bismuth SSP 6c, include a temperature of about −78 degrees Celsius to about 200 degrees Celsius, utilization of suitable solvents such as hexane, pentane, diethylether, and THF. Purification of the SSPs 6f, 6e, 6d, and 6c utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 6f, 6e, 6d, and 6c in Scheme 6.

Figure 9:
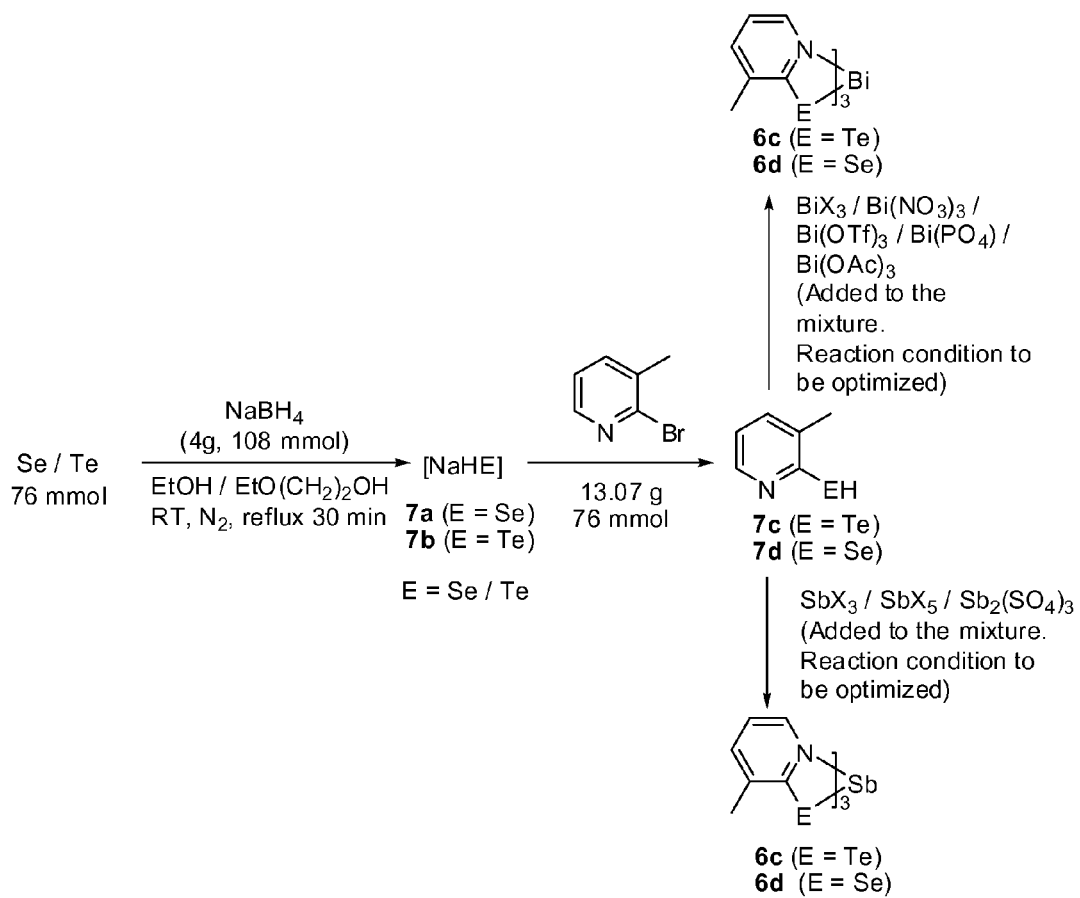
FIG. 9 depicts a scheme (Scheme 7) for forming a single source precursor in accordance with some embodiments of the present disclosure.

In some embodiments, the SSP described above is formed via Scheme 7, as depicted in FIG. 9.

As depicted in Scheme 7 (FIG. 9), a mixture comprising one of selenium or tellurium and $NaBH_4$ is used to form a first intermediary compound of either sodium hydrogen selenium 7a or of sodium hydrogen tellurium 7b. As described in Scheme 7, the first intermediary compounds 7a, 7b can be used to form either a second intermediary compound of either tellurolate 7c or selenolate 7d. One of $SbX_3$, $SbX_5$, $Sb_2(SO_4)_3$ is added to either the lithium tellurolate 7c or the lithium selenolate 7d to form a tellurolate antimony SSP 6e or a selenolate antimony SSP 6f respectively. One of $BiX_3$, $Bi(NO_3)_3$, $Bi(OTf)_3$, $Bi(PO_4)$, $Bi(OAc)_3$ is added to either the lithium tellurolate 7c or the lithium selenolate 7d to form a tellurolate bismuth SSP 6c or a selenolate bismuth SSP 6d respectively. The inventors have observed that suitable reaction conditions for the formation of the selenolate antimony SSP 6f, the tellurolate antimony SSP 6e, the selenolate bismuth SSP 6d, and the tellurolate bismuth SSP 6c, include a temperature of about −78 degrees Celsius to about 200 degrees Celsius, utilization of suitable solvents such as hexane, pentane, diethylether, and THF. Purification of the SSPs 6f, 6e, 6d, and 6c utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 6f, 6e, 6d, and 6c in Scheme 7.

The following formula depicts a single source precursor (SSP) in accordance with some embodiments of the present disclosure:

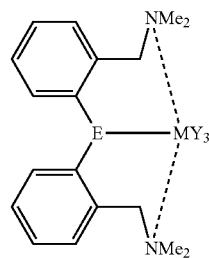

Figure 10:
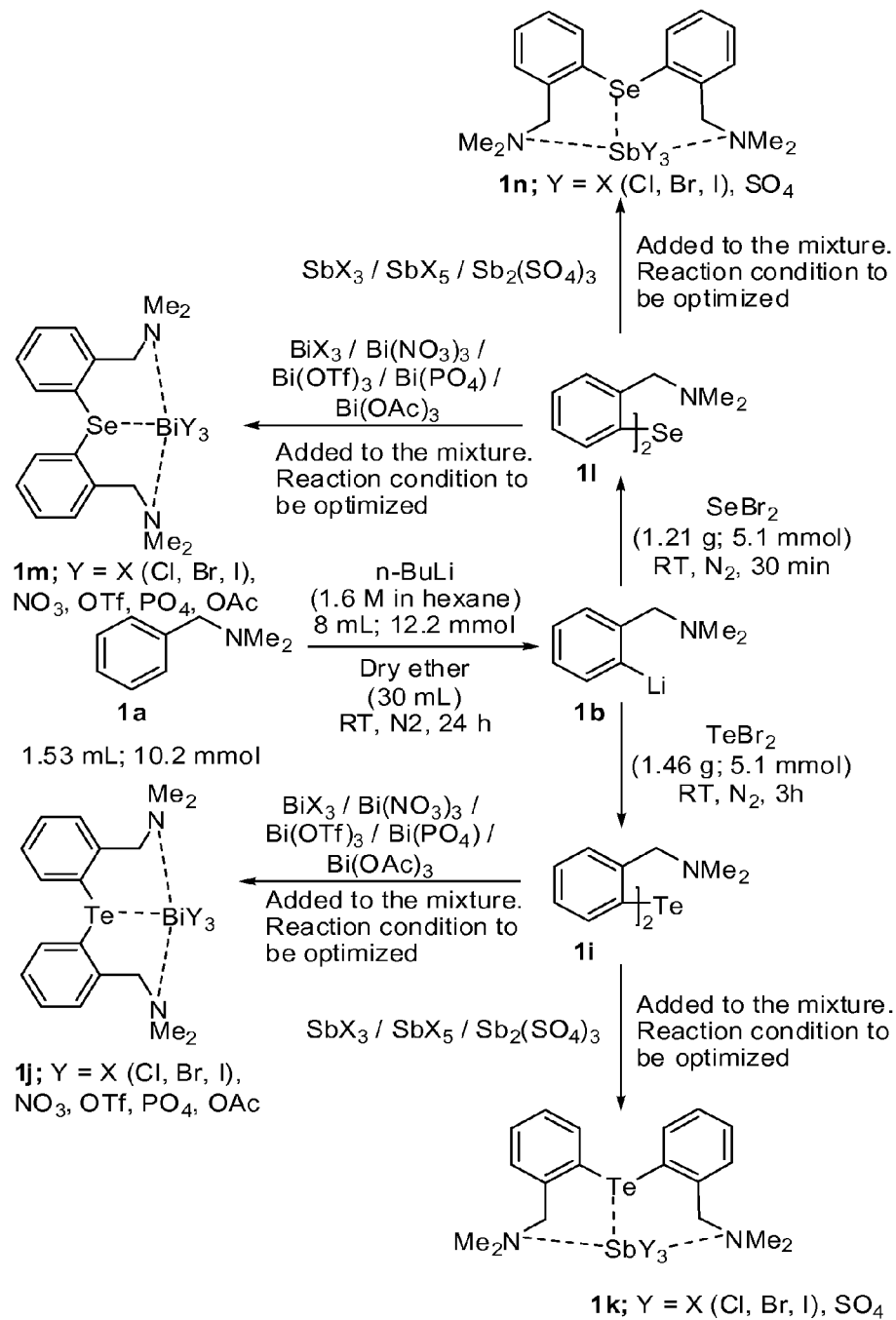
FIG. 10 depicts a scheme (Scheme 8) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or $SO_4$. In embodiments, where E is one of tellurium (Te) or selenium (Se) and M is bismuth (Bi), Y is one of a halogen (i.e. Cl, Br, I), $NO_3$, OTf, $PO_4$, or OAc. In some embodiments, the SSP described above is formed via Scheme 8, as depicted in FIG. 10.

As depicted in Scheme 8 (FIG. 10), a starting compound 1a is used to form intermediary compound 1b. Starting compound 1a is a commercially available N,N-dimethylbenzenemethanamine. Intermediary compound 1b is 2-lithium-N,N-dimethylbenzenemethanamine. As described in Scheme 8, intermediary compound 1b can be used to form either monoselenide 1l or monotelluride 1i. Monoselenide 1l is formed as shown in Scheme 8 via the addition of selenium bromide ($SeBr_2$) to intermediary compound 1b. Monotelluride 1i is formed as shown in Scheme 8 via the addition of tellurium bromide (TeBr$_2$) to intermediary compound 1b. One of SbX$_3$, SbX$_5$, Sb$_2$(SO$_4$)$_3$ is added to the monoselenide 1l to form a selenolate antimony SSP 1n. One of SbX$_3$, SbX$_5$, Sb$_2$(SO$_4$)$_3$ is added to the monotelluride to form a tellurolate antimony SSP 1k. One of BiX$_3$, Bi(NO$_3$)$_3$, Bi(OTf)$_3$, Bi(PO$_4$), Bi(OAc)$_3$ is added to the monoselenide 1l to form a selenolate bismuth SSP 1m. One of BiX$_3$, Bi(NO$_3$)$_3$, Bi(OTf)$_3$, Bi(PO$_4$), Bi(OAc)$_3$ is added to the monotelluride to form a tellurolate bismuth SSP 1j. The inventors have observed that suitable reaction conditions for the formation of the above SSPs 1m, 1n, 1j, 1k include a temperature of about −78 degrees Celsius to about 200 degrees Celsius, utilization of suitable solvents such as hexane, pentane, diethylether, and THF. Purification of the SSPs 1m, 1n, 1j, 1k utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 1m, 1n, 1j, 1k in Scheme 8.

The following formula depicts a single source precursor (SSP) in accordance with some embodiments of the present disclosure:

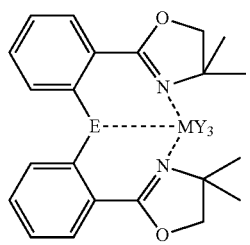

Figure 11:
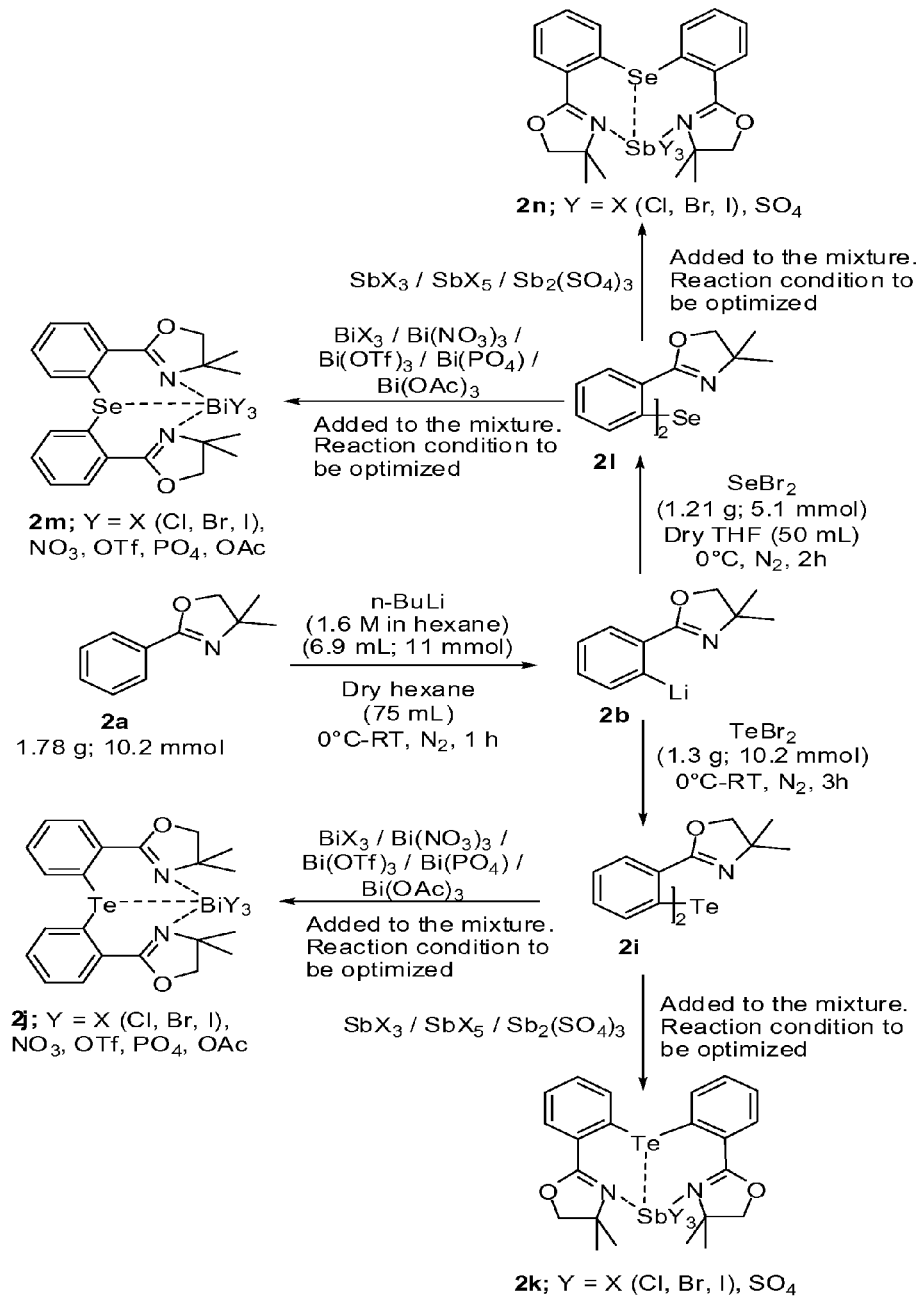
FIG. 11 depicts a scheme (Scheme 9) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or SO$_4$. In embodiments, where E is one of tellurium (Te) or selenium (Se) and M is bismuth (Bi), Y is one of a halogen (i.e. Cl, Br, I), NO$_3$, OTf, PO$_4$, or OAc. In some embodiments, the SSP described above is formed via Scheme 9, as depicted in FIG. 11.

As depicted in Scheme 9 (FIG. 11), a starting compound 2a is used to form intermediary compound 2b. Starting compound 2a is a commercially available 4,5-dihydro-4,4-dimethyl-2-phenyl-oxazole. Intermediary Compound 2b is [2-(4,5-dihydro-4,4-dimethyl-2-oxazolyl)phenyl] lithium. As described in Scheme 9, intermediary compound 2b can be used to form either monoselenide 2l or monotelluride 2i. Monoselenide 2l is formed as shown in Scheme 9 via the addition of selenium bromide (SeBr$_2$) to intermediary compound 2b. Monotelluride 2i is formed as shown in Scheme 9 via the addition of tellurium bromide (TeBr$_2$) to intermediary compound 2b. One of SbX$_3$, SbX$_5$, Sb$_2$(SO$_4$)$_3$ is added to the monoselenide 2l to form a selenolate antimony SSP 2n. One of SbX$_3$, SbX$_5$, Sb$_2$(SO$_4$)$_3$ is added to the monotelluride 2i to form a tellurolate antimony SSP 2k. One of BiX$_3$, Bi(NO$_3$)$_3$, Bi(OTf)$_3$, Bi(PO$_4$), Bi(OAc)$_3$ is added to the monoselenide 2l to form a selenolate bismuth SSP 2m. One of BiX$_3$, Bi(NO$_3$)$_3$, Bi(OTf)$_3$, Bi(PO$_4$), Bi(OAc)$_3$ is added to the monotelluride 2i to form a tellurolate bismuth SSP 2j. The inventors have observed that suitable reaction conditions for the formation of the above SSPs 2m, 2n, 2j, 2k include a temperature of about −78 degrees Celsius to about 200 degrees Celsius, utilization of suitable solvents such as hexane, pentane, diethylether, and THF. Purification of the SSPs 2m, 2n, 2j, 2k utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 2m, 2n, 2j, 2k in Scheme 9.

The following formula depicts a single source precursor (SSP) in accordance with some embodiments of the present disclosure:

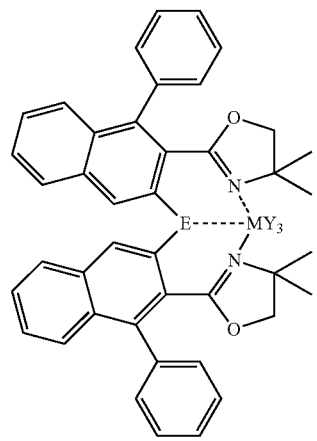

Figure 12:
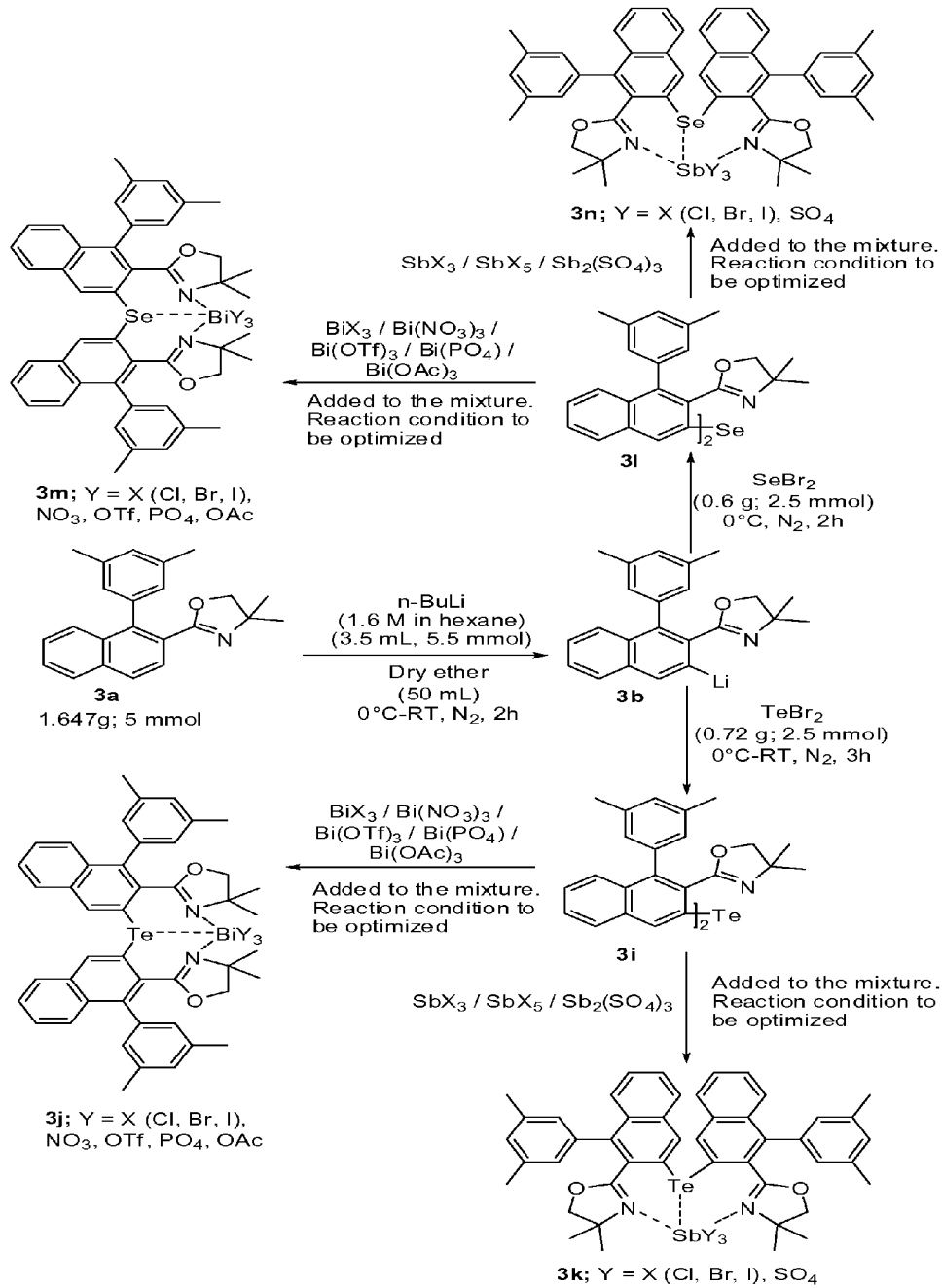
FIG. 12 depicts a scheme (Scheme 10) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or SO$_4$. In embodiments, where E is one of tellurium (Te) or selenium (Se) and M is bismuth (Bi), Y is one of a halogen (i.e. Cl, Br, I), NO$_3$, OTf, PO$_4$, or OAc. In some embodiments, the SSP described above is formed via Scheme 10, as depicted in FIG. 12.

As depicted in Scheme 10 (FIG. 12), a starting compound 3a is used to form intermediary compound 3b. Starting compound 3a is commercially available 2-[1-(3,5-dimethylphenyl)-2-naphthalenyl]-4,5-dihydro-4,4-dimethyl-oxazole. Intermediary compound 3b is 2-[2-[1-(3,5-dimethylphenyl)-2-naphthalenyl]-4,5-dihydro-4,4-dimethyl-oxazolyl)phenyl] lithium. As described in Scheme 10, intermediary compound 3b can be used to form either monoselenide 3l or monotelluride 3i. Monoselenide 3l is formed as shown in Scheme 10 via the addition of selenium bromide (SeBr$_2$) to intermediary compound 3b. Monotelluride 3i is formed as shown in Scheme 10 via the addition of tellurium bromide (TeBr$_2$) to intermediary compound 3b. One of SbX$_3$, SbX$_5$, Sb$_2$(SO$_4$)$_3$ is added to the monoselenide 3l to form a selenolate antimony SSP 3n. One of SbX$_3$, SbX$_5$, Sb$_2$(SO$_4$)$_3$ is added to the monotelluride 3i to form a tellurolate antimony SSP 3k. One of BiX$_3$, Bi(NO$_3$)$_3$, Bi(OTf)$_3$, Bi(PO$_4$), Bi(OAc)$_3$ is added to the monoselenide 3l to form a selenolate bismuth SSP 3m. One of BiX$_3$, Bi(NO$_3$)$_3$, Bi(OTf)$_3$, Bi(PO$_4$), Bi(OAc)$_3$ is added to the monotelluride 3i to form a tellurolate bismuth SSP 3j. The inventors have observed that suitable reaction conditions for the formation of the above SSPs 3m, 3n, 3j, 3k include a temperature of about −78 degrees Celsius to about 200 degrees Celsius, utilization of suitable solvents such as hexane, pentane, diethylether, and THF. Purification of the SSPs 3m, 3n, 3j, 3k utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 3m, 3n, 3j, 3k in Scheme 10.

The following formula depicts a single source precursor (SSP) in accordance with some embodiments of the present disclosure:

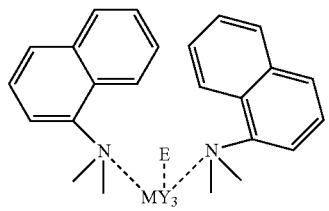

Figure 13:
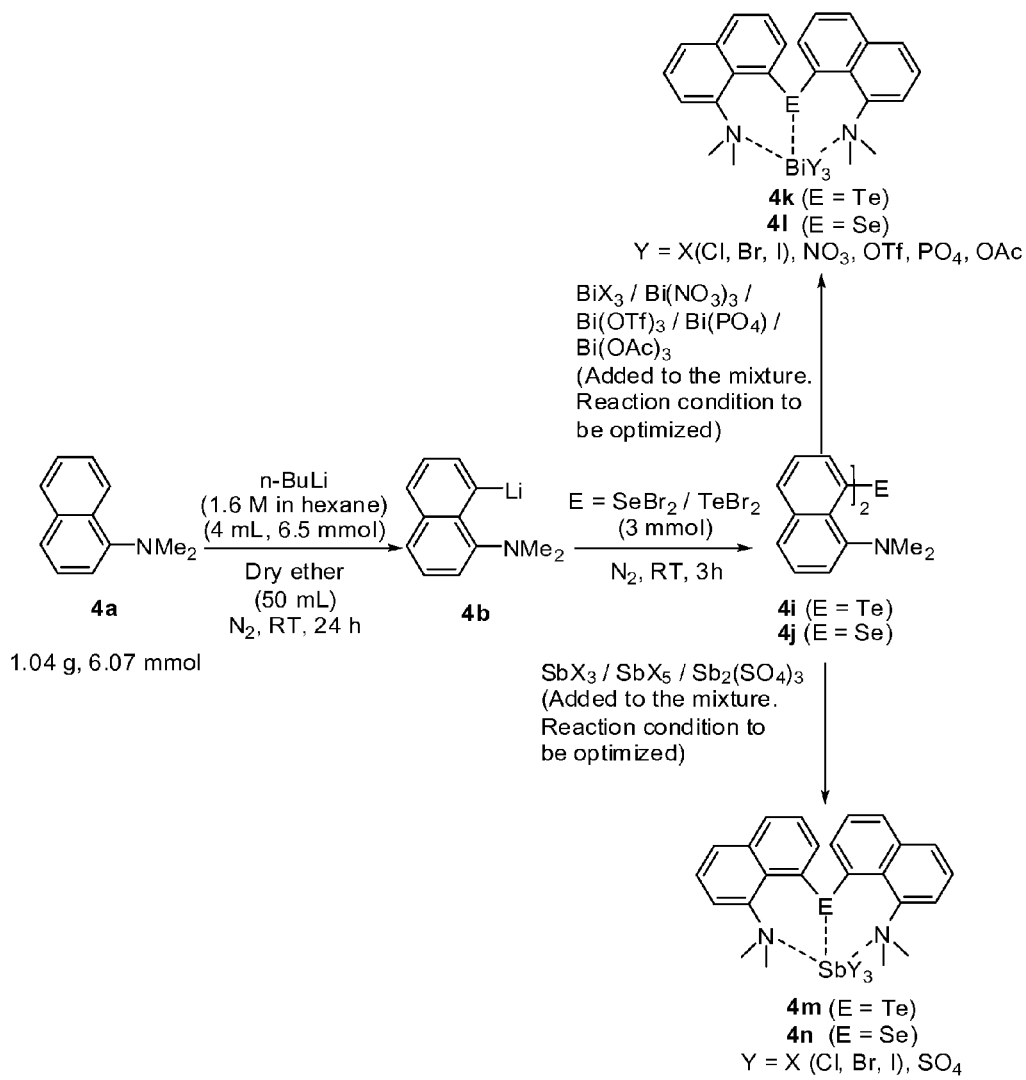
FIG. 13 depicts a scheme (Scheme 11) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or $SO_4$. In embodiments, where E is one of tellurium (Te) or selenium (Se) and M is bismuth (Bi), Y is one of a halogen (i.e. Cl, Br, I), $NO_3$, OTf, $PO_4$, or OAc. In some embodiments, the SSP described above is formed via Scheme 11, as depicted in FIG. 13.

As depicted in Scheme 11 (FIG. 13), a starting compound 4a is used to form intermediary compound 4b. Starting compound 4a is commercially available N, N-dimethyl-1-naphthanamine. Intermediary compound 4b is (8-dimethylamino)-1-naphthyllithium. As described in Scheme 11, intermediary compound 4b can be used to form either monoselenide 4j or monotelluride 4i. Monoselenide 4j is formed as shown in Scheme 11 via the addition of selenium bromide ($SeBr_2$) to intermediary compound 4b. Monotelluride 3i is formed as shown in Scheme 11 via the addition of tellurium bromide ($TeBr_2$) to intermediary compound 4b. One of $SbX_3$, $SbX_5$, $Sb_2(SO_4)_3$ is added to either the monoselenide 4j or monotelluride 4i to form a selenolate antimony SSP 4n or a tellurolate antimony SSP 4m respectively. One of $BiX_3$, $Bi(NO_3)_3$, $Bi(OTf)_3$, $Bi(PO_4)$, $Bi(OAc)_3$ is added to either the monotelluride 4i or monoselenide 4j to form a tellurolate bismuth SSP 4k or a selenolate bismuth SSP 4l respectively. The inventors have observed that suitable reaction conditions for the formation of the SSPs 4m, 4n, 4k, 4l, include a temperature of about −78 degrees Celsius to about 200 degrees Celsius, utilization of suitable solvents such as hexane, pentane, diethylether, and THF. Purification of the SSPs 4m, 4n, 4k, 4l utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 4m, 4n, 4k, 4l in Scheme 11.

The following formula depicts a single source precursor (SSP) in accordance with some embodiments of the present disclosure:

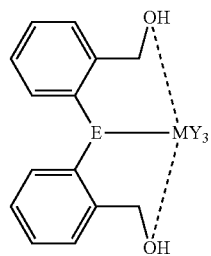

Figure 14:
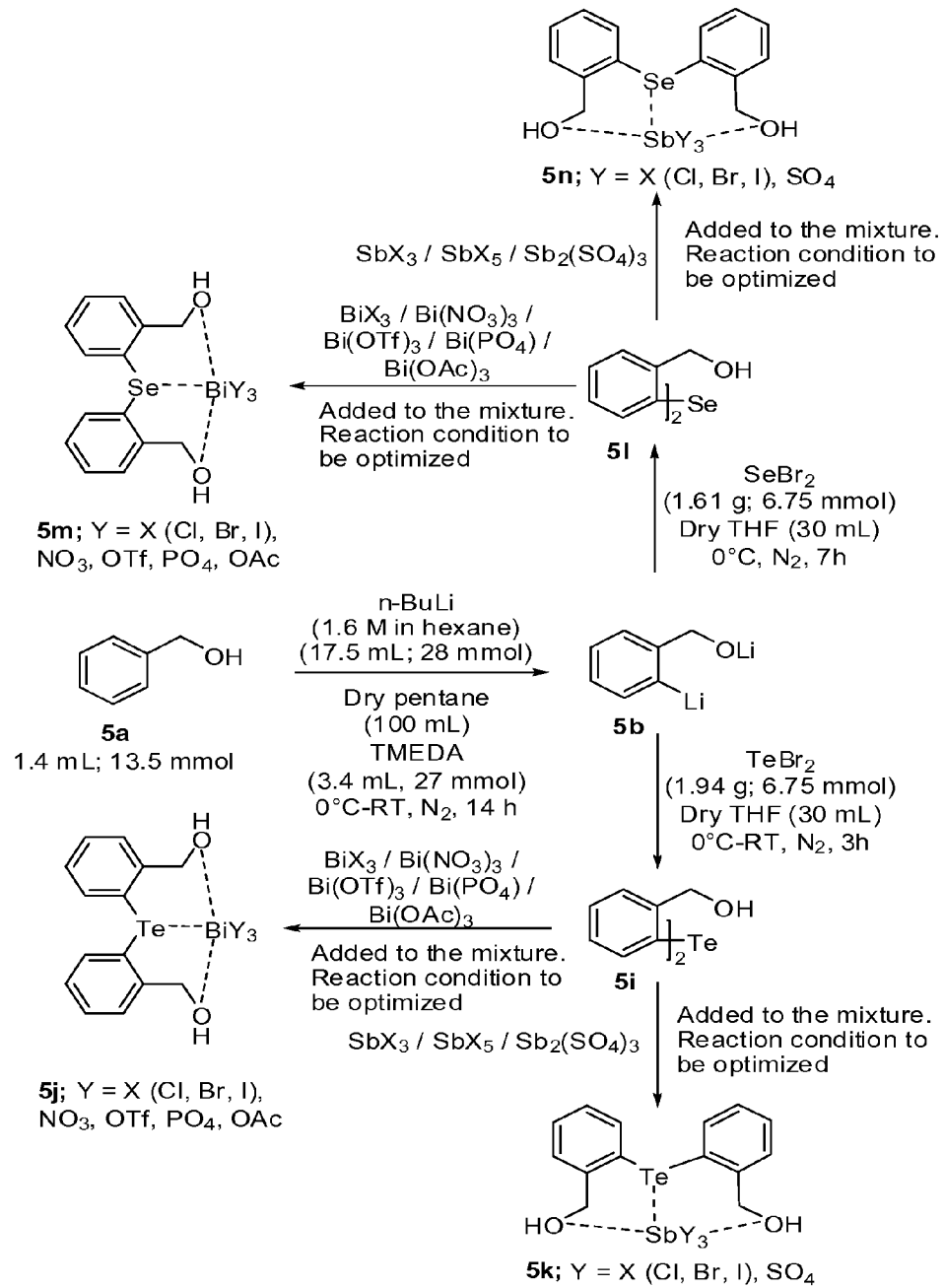
FIG. 14 depicts a scheme (Scheme 12) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or $SO_4$. In embodiments, where E is one of tellurium (Te) or selenium (Se) and M is bismuth (Bi), Y is one of a halogen (i.e. Cl, Br, I), $NO_3$, OTf, $PO_4$, or OAc. In some embodiments, the SSP described above is formed via Scheme 12, as depicted in FIG. 14.

As depicted in Scheme 12 (FIG. 14), a starting compound 12a is used to form intermediary compound 12b. Starting compound 12a is commercially available benzyl alcohol. Intermediary compound 12b is lithium salt of [2-(hydroxymethyl) phenyl] lithium. As described in Scheme 12, intermediary compound 12b can be used to form either monoselenide 5l or monotelluride 5i. Monoselenide 5l is formed as shown in Scheme 12 via the addition of selenium bromide ($SeBr_2$) to intermediary compound 5b. Monotelluride 5i is formed as shown in Scheme 12 via the addition of tellurium bromide ($TeBr_2$) to intermediary compound 5b. One of $SbX_3$, $SbX_5$, $Sb_2(SO_4)_3$ is added to the monoselenide 5l to form a selenolate antimony SSP 5n. One of $SbX_3$, $SbX_5$, $Sb_2(SO_4)_3$ is added to the monotelluride 5i to form a tellurolate antimony SSP 5k. One of $BiX_3$, $Bi(NO_3)_3$, $Bi(OTf)_3$, $Bi(PO_4)$, $Bi(OAc)_3$ is added to the monoselenide 5l to form a selenolate bismuth SSP 5m. One of $BiX_3$, $Bi(NO_3)_3$, $Bi(OTf)_3$, $Bi(PO_4)$, $Bi(OAc)_3$ is added to the monotelluride 5i to form a tellurolate bismuth SSP 5j. The inventors have observed that suitable reaction conditions for the formation of the above SSPs 5m, 5n, 5j, 5k include a temperature of about −78 degrees Celsius to about 200 degrees Celsius, utilization of suitable solvents such as hexane, pentane, diethylether, and THF. Purification of the SSPs 5m, 5n, 5j, 5k utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 5m, 5n, 5j, 5k in Scheme 12.

The following formula depicts a single source precursor (SSP) in accordance with some embodiments of the present disclosure:

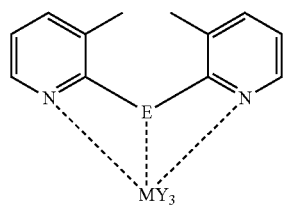

Figure 15:
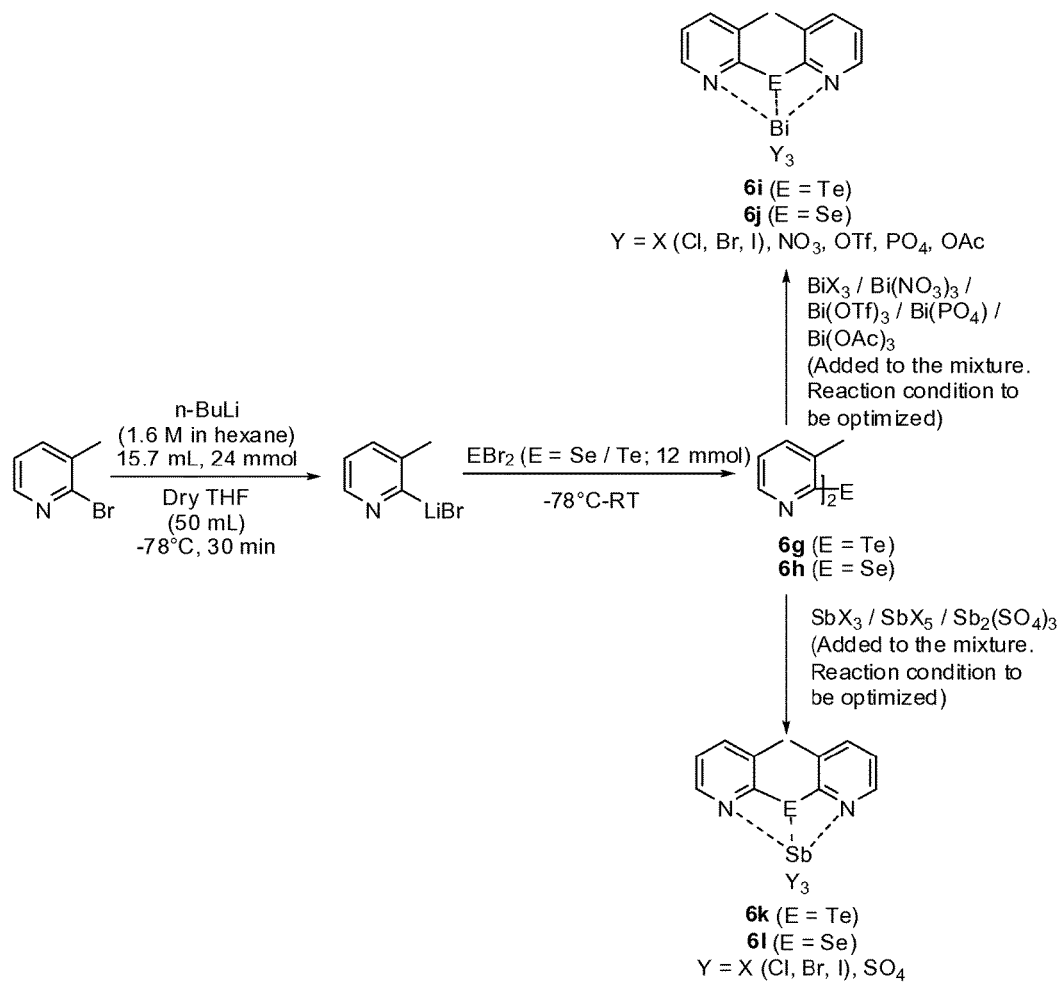
FIG. 15 depicts a scheme (Scheme 13) for forming a single source precursor in accordance with some embodiments of the present disclosure.

In some embodiments, E is one of tellurium (Te) or selenium (Se) and M is one of bismuth (Bi) or antimony (Sb). In embodiments, where E is one of tellurium (Te) or selenium (Se) and M is antimony (Sb), Y is one of a halogen (i.e. Cl, Br, I) or SO$_4$. In embodiments, where E is one of tellurium (Te) or selenium (Se) and M is bismuth (Bi), Y is one of a halogen (i.e. Cl, Br, I), NO$_3$, OTf, PO$_4$, or OAc. In some embodiments, the SSP described above is formed via Scheme 13, as depicted in FIG. 15.

As depicted in Scheme 13 (FIG. 15), a starting compound 6a is used to form intermediary compound 6b. Starting compound 6a is commercially available 2-bromo-3-methyl-pyridine. Intermediary compound 6b is (2-bromo-3-pyridinyl)-lithium. 6a is commercially available. As described in Scheme 13, intermediary compound 6b can be used to form either monoselenide 6h or monotelluride 6g. Monoselenide 6h is formed as shown in Scheme 13 via the addition of selenium bromide (SeBr$_2$) to intermediary compound 6b. Monotelluride 6g is formed as shown in Scheme 13 via the addition of tellurium bromide (TeBr$_2$) to intermediary compound 6b. One of SbX$_3$, SbX$_5$, Sb$_2$(SO$_4$)$_3$ is added to either the monoselenide 6h or monotelluride 6g to form a selenolate antimony SSP 6l or a tellurolate antimony SSP 6k respectively. One of BiX$_3$, Bi(NO$_3$)$_3$, Bi(OTf)$_3$, Bi(PO$_4$), Bi(OAc)$_3$ is added to either the monotelluride 6g or monoselenide 6h to form a tellurolate bismuth SSP 6i or a selenolate bismuth SSP 6j respectively. The inventors have observed that suitable reaction conditions for the formation of the SSPs 6i, 6j, 6l, 6k, include a temperature of about −78 degrees Celsius to about 200 degrees Celsius, utilization of suitable solvents such as hexane, pentane, diethylether, and THF. Purification of the SSPs 6i, 6j, 6l, 6k utilizes solvents such as chloroform, dichloromethane, carbon tetrachloride, toluene, xylenes, methanol, ethanol, hexane, pentane, diethylether, THF and the like at temperatures ranging from −40 degrees Celsius to room temperature (e.g. about 25 degrees Celsius) and under a nitrogen-argon atmosphere or ambient atmosphere to prevent decomposition of the SSPs 6i, 6j, 6l, 6k, in Scheme 13.

As depicted in Schemes 1-13 (FIGS. 3-15), a method of forming a single source precursor described above comprises mixing a first compound with one of one of SbX$_3$, SbX$_5$, Sb$_2$(SO$_4$)$_3$ or with one of BiX$_3$, Bi(NO$_3$)$_3$, Bi(OTf)$_3$, Bi(PO$_4$), Bi(OAc)$_3$. The first compound is one of a lithium selenolate, a lithium tellurolate, a monoselenide, or a monotelluride.

For example, in some embodiments the lithium selenolate has one of the following formulas:

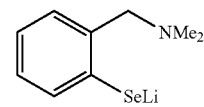

(a)

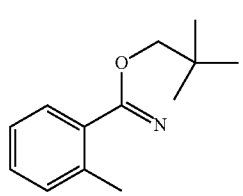

(b)

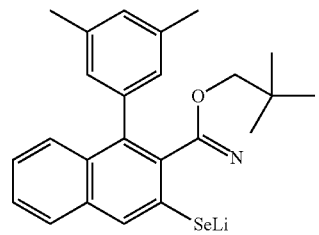

(c)

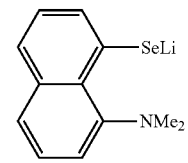

(d)

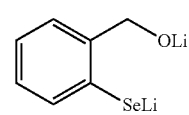

(e)

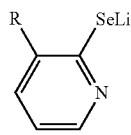

(f)

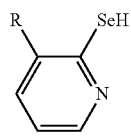

(g)

wherein R is one of hydrogen or an alkyl having the general formula C$_n$H$_{2n+1}$ and n is a whole number, such as methyl, CH$_3$, ethyl (C$_2$H$_5$), propyl (C$_3$H$_7$), butyl (C$_4$H$_9$), pentyl (C$_5$H$_{11}$), or the like.

For example, the lithium tellurolate has one of the following formulas:

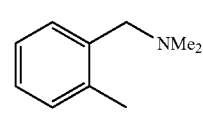

(a)

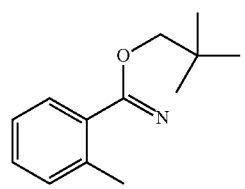

(b)

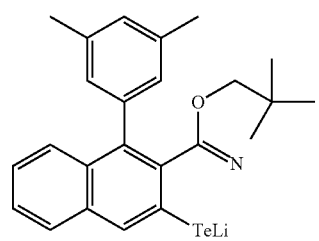

(c)

-continued

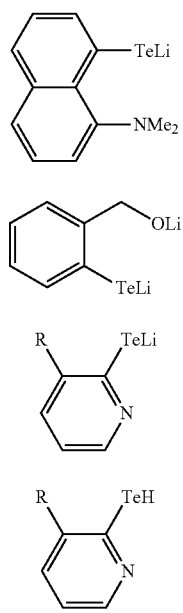

(d)

(e)

(f)

(g)

wherein R is one of hydrogen or an alkyl having the general formula $C_nH_{2n+1}$ and n is a whole number, such as methyl, $CH_3$, ethyl ($C_2H_5$), propyl ($C_3H_7$), butyl ($C_4H_9$), pentyl ($C_5H_{11}$), or the like.

For example, in some embodiments the monoselenide has one of the following formulas:

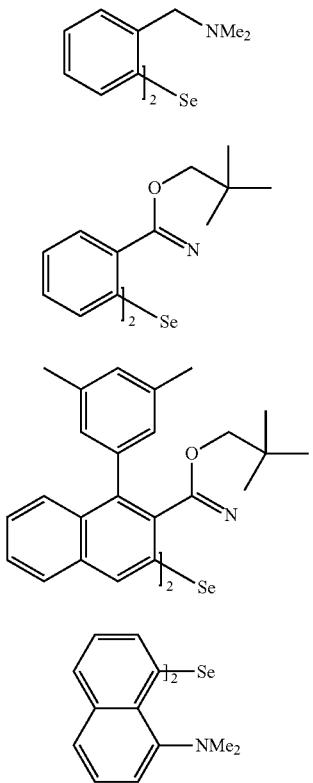

(a)

(b)

(c)

(d)

(e)

(f)

For example, the monotelluride has one of the following formulas:

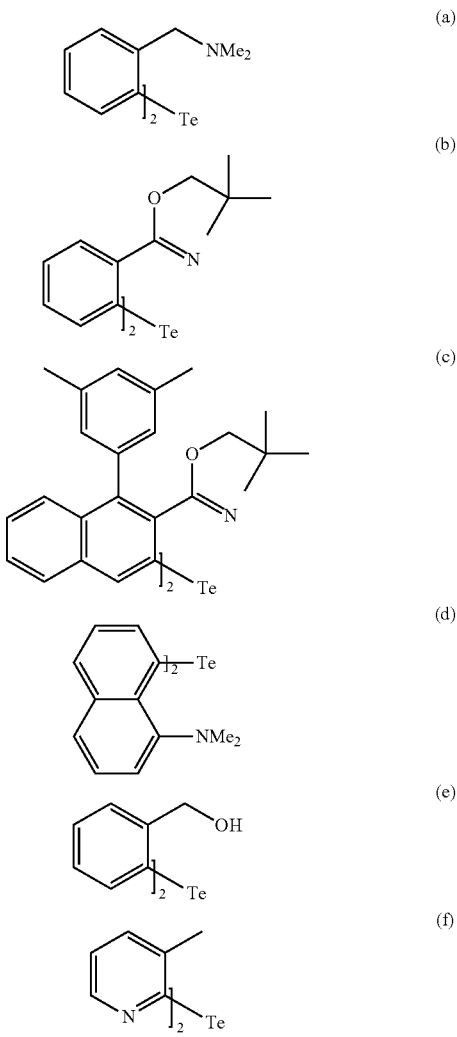

(a)

(b)

(c)

(d)

(e)

(f)

While the synthesis method described above is shown for bismuth tellurium ($Bi_2Te_3$), bismuth selenium ($Bi_2Se_3$), antimony selenium ($Sb_2Se_3$) and antimony tellurium ($Sb_2Te_3$) a person of ordinary skill in the art may synthesize other thermoelectric material of interest, including PbTe, PbTe, $La_2Te_3$, $CoSb_3$, SiGe, $Mg_2SiSn$, BiSbTe, YbMnSb, BaYbCoSb, using the synthesis scheme disclosed above.

FIG. 1 is a flow diagram of a method 100 for depositing thin films either in planar structures or in nanowires form using the single source precursors described above in accordance with some embodiments of the present disclosure.

Nanowire based thin film devices of thermoelectric devices provide an improved figure of merit compared to devices made with bulk powders. The advantages of using nanowires for thermoelectric devices includes: enhanced density of states due to quantum confinement effects (i.e. increase S without reducing σ), boundary scattering at interfaces can reduce k more than σ, possibility of materials engineering to further improve ZT, photon blocking/electron transmitting superlattices, which utilize the acoustic mismatch between superlattice components to reduce the lattice thermal conductivity (core-shell NWs concept), and thermionic effects in heterostructures to improve the figure of merit. Electrospinning to deposit thin films is advantageously a cost effective and simple technique to create aligned nanowires, resulting in improved efficiency and lower cost of the final device.

The method 100 begins at step 102, wherein a liquid polymer precursor material is flowed through an orifice spaced apart from a substrate upon which the liquid polymer precursor material is to be deposited.

The liquid polymer precursor material comprises a polymer dissolved in a solvent. The selection of the polymer depends on the solubility of the high molecular weight polymer in polar organic solvents. In some embodiments, suitable polymers include polyethylene oxide (PEO), polyethylene glycol (PEG), polyvinyl alcohol (PVA), polyvinyl pyridine (PVP), polyacrylnitrile (PAN), polymethacrylate, Polyacrylamide, Polyvinylchloride, poly vinyl phenol, polyamide, polyacrylic acid, polyaniline or the like. In some embodiments, suitable solvents include polar organic solvents such as dimethyl sulfoxide (DMSO), tetrahydrofuran (THF), diethyl acetamide, dichloromethane, chloroform, dimethyl acetamide, dimethyl formamide, methylene chloride, carbon disulfide, toluene, formic acid, camphorsulphonic acid, or the like. In addition, alcohols such as methanol, iso-propanol, ethanol or the like can also be added to the above polar organic solvent to increase the solubility of the polymer.

The single source precursors synthesized in schemes 1-13 (FIGS. 3-15) are mostly solid and/or semi-solid and thus need to be dissolved. As such, after the polymer is dissolved in the solvent, the single source precursor is dissolved in the liquid polymer precursor solution. The liquid polymer precursor solution is stirred for about 24 to about 72 hours to obtain a uniform solution. In some embodiments, a reducing agent may be added to the liquid polymer precursor solution to help reduce the precursors into their metallic form. In some embodiments, the polymer concentration in the solution is about 20% to about 95% by volume with the balance (i.e. about 80% to about 5% by volume) being the single source precursor concentration.

The liquid polymer precursor material may be pumped through the orifice to provide a predetermined flow rate, diameter of the liquid polymer precursor material exiting the orifice, or the like. The substrate may be, for example, a semiconductor substrate, a glass panel, or part of an electronic device being fabricated on the substrate.

The method 100 continues at step 104, wherein a potential difference is created between the orifice and the substrate to attract the liquid polymer precursor material towards the substrate, thereby forming a deposited material on the substrate. In some embodiments, the deposited material may be in the form of nanofibers. In some embodiments, the nanofibers are smooth and uniform. The orifice and the substrate may be moved relative to each other to control the properties and distribution of the deposited material on the substrate, as discussed below.

Variable sized orifices can be used to obtain variable sized nanowires. Other variables in the deposition process include the distance between the orifice and the substrate, the concentration of the polymer and the single source precursor, the applied voltage, the solution feed rate (nl/min to ml/min), and the deposition time. In some embodiments, the voltage is about 5 kV to about 30 kV with a DC power supply. In some embodiments, the distance between the orifice and substrate is about 5 cm to about 25 cm. In some embodiments, polymer concentration in the liquid polymer solution is about 20% to about 95% and the single source precursor concentration in the liquid polymer solution is about 5% to about 80%. In some embodiments, the size of orifice, which may be a syringe needle gauge, can be about 16 G to about 28 G.

In some embodiments, an AC voltage is applied across the substrate. In some embodiments, the voltage can be varied from about +/−6V to about 24V. By applying an AC voltage to the substrate the fibers generated from the orifice due to the high voltage will be drawn to the +/− ends of the electrode on the substrate and will create an aligned network of nanofibers. Aligned nanowires may also be formed by placing an interdigitated mask on the substrate and confining the voltage along the path of the electrode.

The method 100 generally concludes at step 106, wherein the deposited material is cured to remove polymer from the deposited film on the substrate. The polymer is removed by thermal treatment at temperatures about 200 to about 500 degrees Celsius for about 0.5 to about 1 hour.

In some embodiments, polymer removal can be accomplished by transferring the substrate to a hot wire chemical vapor deposition (HWCVD) chamber. In a HWCVD chamber, filaments composed of, for example tungsten or titanium, are heated to temperature of about 1000 to about 2400 degrees Celsius. Hydrogen gas is introduced into the HWCVD chamber and decomposed by the heated filaments to generate atomic hydrogen (i.e. hydrogen radicals) which reach the substrate and remove polymer and other carbon elements present on the substrate. In some embodiments the substrate is maintained at a temperature of about 200 to about 400 degrees Celsius. Upon removing the polymer, the final product will be nanowires composed of single source precursor material (i.e. bismuth tellurium ($Bi_2Te_3$), along with bismuth selenium ($Bi_2Se_3$), antimony tellurium ($Sb_2Te_3$) and antimony selenium ($Sb_2Se_3$)).

In some embodiments, polymer can be removed from the deposited film on the substrate by using a wet etch method. In such embodiments, the deposited film is exposed to solvents, reducing agents, and or oxidizing agents in which the polymer dissolves easily, such as acetonitrile, THF, DMF, heptane, chloroform, dichlorobenzene, toluene, dichloromethane, benzene, or the like. The heating temperature depends on the boiling point of the solvent being used. The heating can be done up to the boiling temperature of the particular solvent or mixture of solvents being used.

Figure 2:
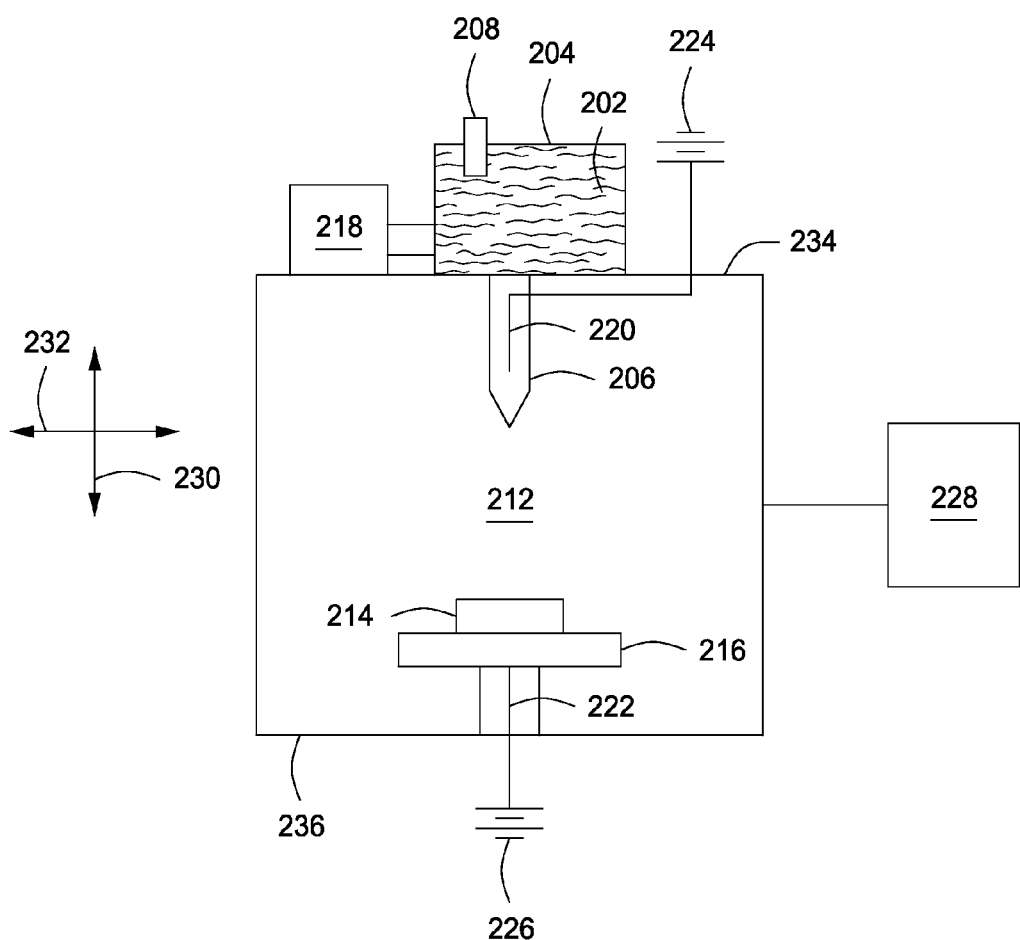
FIG. 2 depicts an apparatus equipped to deposit polymer films in accordance with some embodiments of the present disclosure.

FIG. 2 depicts an equipped to deposit polymer films in accordance with some embodiments of the present disclosure. The apparatus 200 includes a chamber body 210 defining an inner volume 212; a reservoir 204 coupled to the chamber body 210; an orifice 206 coupled to the reservoir 204, wherein the orifice 206 projects downward into the inner volume 212 of the chamber body 210; and a substrate 214 disposed upon a substrate support 216 coupled to a bottom wall 236 of the chamber body 210.

In some embodiments, the reservoir 204 is coupled to the upper wall 234 of the chamber body 210. The reservoir 204 holds a liquid polymer precursor material 202 as described above. In some embodiments, the reservoir 204 is a container that may be sealed in a pressure tight manner. In some embodiments, a temperature sensor 208 may be positioned within the reservoir 204 to measure the temperature of the liquid polymer precursor material 202 inside the reservoir 204. In some embodiments, the liquid polymer precursor material 202 may be stored in the reservoir 204 at room temperature. In some embodiments, heating and cooling coils (not shown), carrying a heat transfer fluid, may be wrapped around the exterior of the reservoir 204 to control the temperature and viscosity of the liquid polymer precursor material 202 within the reservoir 204. The heat transfer fluid may be a gas, such as helium (He), oxygen ($O_2$), or the like, or a liquid, such as water, antifreeze, or an alcohol, for example, glycerol, ethylene glycerol, propylene, methanol, or the like.

In some embodiments, an orifice 206 is coupled to the reservoir 204, wherein the orifice 206 projects downward into the inner volume 212 of the chamber body 210. In some embodiments, the orifice 206 is a hollow nozzle, such as a needle, pipette or syringe. In some embodiments, a pump 218 is attached to the reservoir 204 to force liquid polymer precursor material 202 through the orifice 206. In some embodiments, the diameter of the opening of the orifice 206 may be controlled to control the diameter of the nanofibers. In some embodiments, a plurality of orifices may be connected to the reservoir 204.

In some embodiments, the substrate 214 may be a semiconductor substrate, a glass panel, or part of an electronic device being fabricated on the substrate. In some embodiments, the substrate 214 is positioned on a substrate support 216 disposed within the inner volume 212 of the chamber body 210. The substrate 214 is positioned below the orifice 206. The material will be deposited in a droplet-like form on the substrate 214 as the substrate 214 is positioned closer to the orifice 206. The material will be deposited in a fiber-like form on the substrate 214 as the substrate 214 is positioned farther away from the orifice 206.

In some embodiments, the substrate support 216 may include a mechanism that retains or supports the substrate 214 on the surface of the substrate support 216, such as an electrostatic chuck, a vacuum chuck, a substrate retaining clamp, or the like (not shown). In some embodiments, the substrate support 216 may include heating or cooling coils (not shown), carrying a heat transfer fluid as described above, for controlling the substrate temperature.

In some embodiments, the orifice 206 and/or the substrate support 216 may be coupled to a mechanism for moving the orifice 206 and/or the substrate support 216 with respect to each other. For example, a pneumatic, hydraulic, electric, or manually operated actuator, motor, or the like, may be provided in either or both of the orifice 206 and the substrate support 216 to provide either or both of horizontal or vertical motion. For example, in some embodiments, the orifice 206 and/or the substrate support 216 may be movable along the first direction 232 in the horizontal plane such that the material deposited on the substrate from the orifice 206 can be distributed about the substrate disposed on the substrate support. In some embodiments, the orifice 206 and/or the substrate support 216 may be movable along the second direction 230 in the vertical plane, such as along a vertical axis, to control the spacing between the orifice 206 and the substrate support 216.

In some embodiments, the orifice 206 is connected to a first electrode 220 and the substrate support 216 is connected to a second electrode 222. A potential difference between the first electrode and second electrode creates an electrostatic field between the two electrodes 220, 222 which draws liquid polymer precursor material 202 from the reservoir 204 toward the substrate 214. In some embodiments, the first electrode 220 may be connected to a first power source 224. In some embodiments, the second electrode 222 may be connected to a second bias power source 226.

In some embodiments, a controller 228 may be coupled to the apparatus 200 to facilitate control of the apparatus 200. The controller 228 may be one of any form of general-purpose computer processor that can be used in an industrial setting for controlling various chambers and sub-processors. The controller may be control the apparatus as described above to facilitate fabrication of a predetermined material.

While the foregoing is directed to embodiments of the present disclosure, other and further embodiments of the disclosure may be devised without departing from the basic scope thereof.

The invention claimed is:
1. A compound having one of the following formulas:

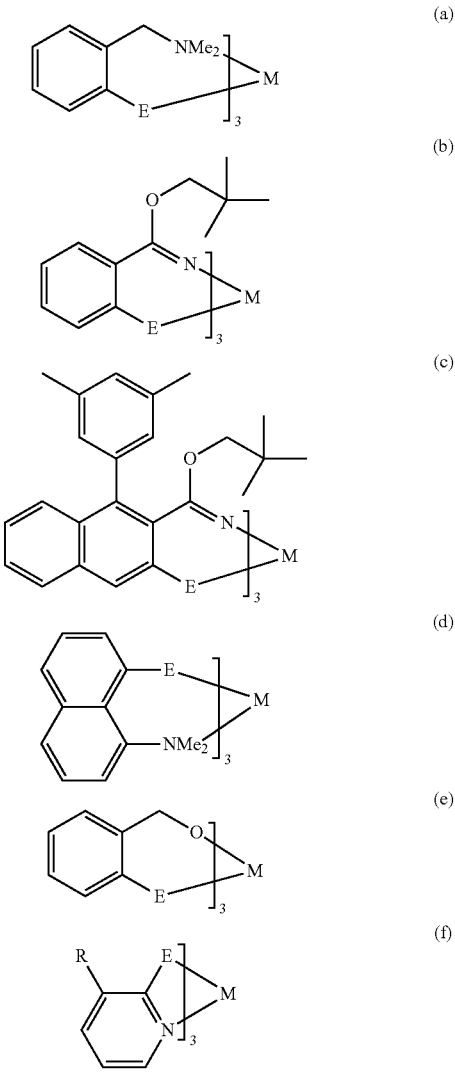

-continued (g)
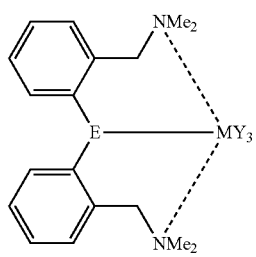

(h)
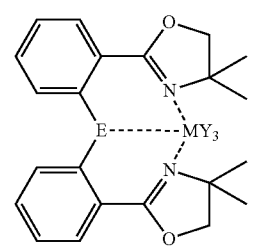

wherein E is one of tellurium (Te) or selenium (Se), M is one of bismuth (Bi) or antimony (Sb), and wherein Y is one of a halogen or SO$_4$ when E is one of tellurium (Te) or selenium (Se) and M is antimony (Sb) or wherein Y is one of a halogen, NO$_3$, triflate (OTf), PO$_4$, or acetoxy (OAc) when E is one of tellurium (Te) or selenium (Se) and M is bismuth (Bi).

2. A method of forming, a compound of claim 1, comprising:

mixing a first compound with one of one of SbX$_3$, SbX$_5$, Sb$_2$(SO$_4$)$_3$ or with one of BiX$_3$, Bi(NO$_3$)$_3$, Bi(OTf)$_3$, Bi(PO$_4$), Bi(OAc)$_3$, wherein the first compound is one of a lithium selenolate, a lithium tellurolate, a monoselenide, or a monotelluride.

3. The method of claim 2, wherein the first compound has one of the following formulas:

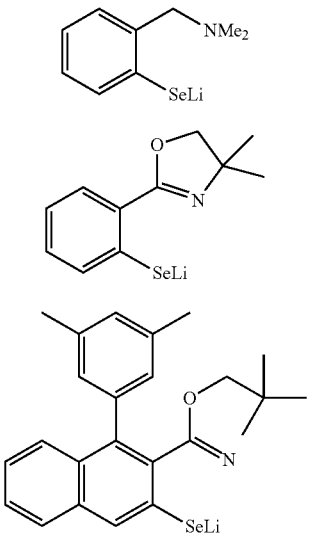

(a)

(b)

(c)

-continued (d)
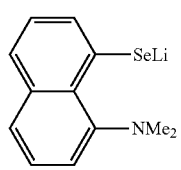

(e)
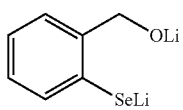

(f)
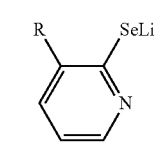

(g)
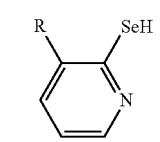

wherein R is one of hydrogen or an alkyl having a general formula C$_n$H$_{2n+1}$, wherein n is a whole number.

4. The method of claim 2, wherein the first compound has one of the following formulas:

(a)
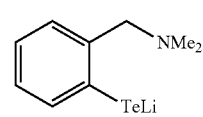

(b)
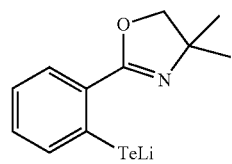

(c)
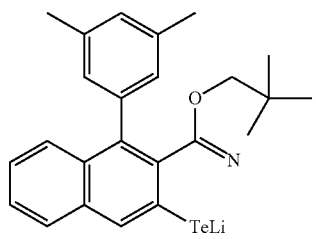

(d)
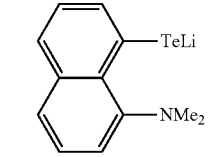

(e)
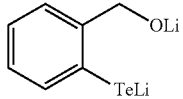

-continued (f) 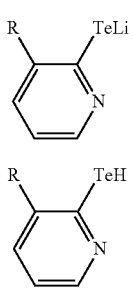

(g)

wherein R is one of hydrogen or an alkyl having a general formula $C_nH_{2n+1}$, wherein n is a whole number.

5. The method of claim 2, wherein the monoselenide has one of the following formulas:

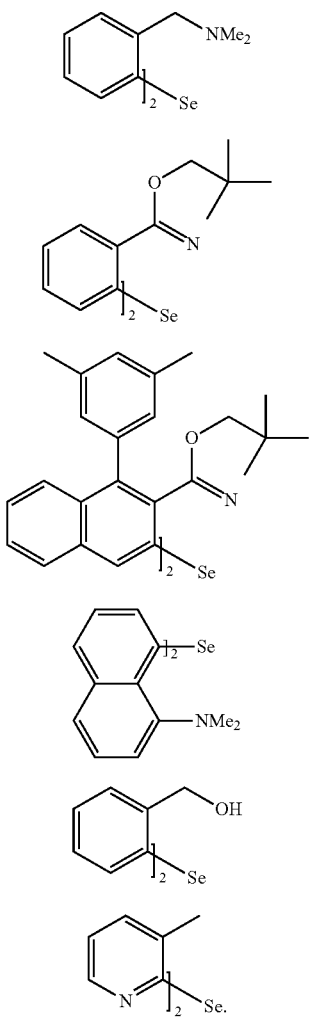

6. The method of claim 2, wherein the monotelluride has one of the following formulas:

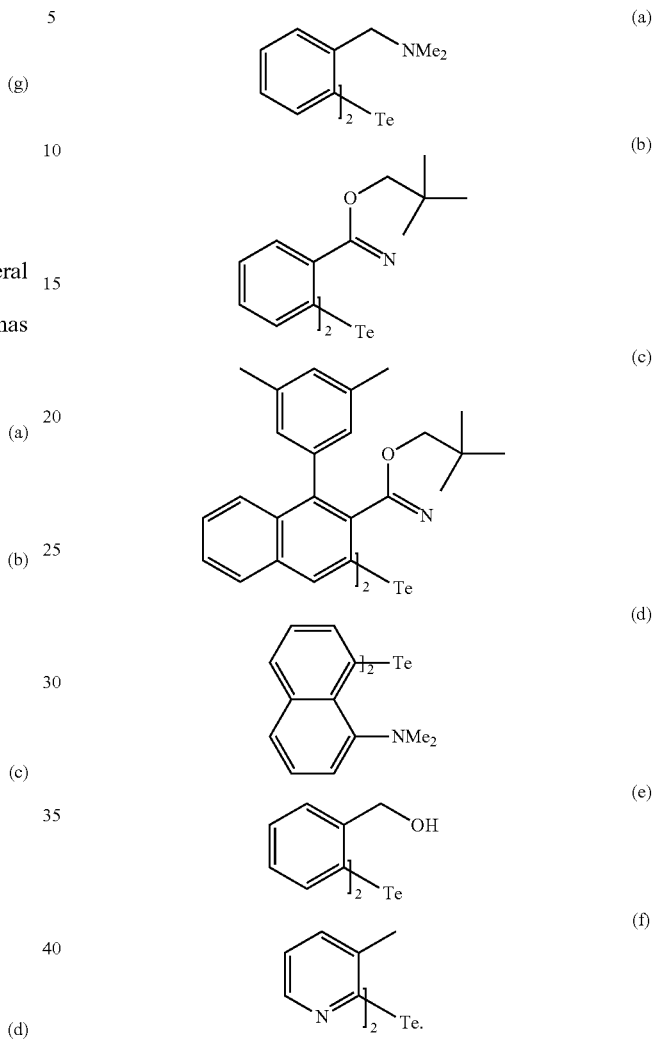

7. A compound having the formula:

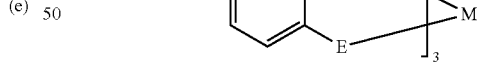

wherein E is one of tellurium (Te) or selenium (Se), M is one of bismuth (Bi) or antimony (Sb).

8. The compound of claim 7, wherein E is tellurium.
9. The compound of claim 7, wherein E is selenium.
10. The compound of claim 7, wherein M is bismuth.
11. The compound of claim 7, wherein M is antimony.

* * * * *